US012611353B2

(12) United States Patent
Huang et al.

(10) Patent No.: US 12,611,353 B2
(45) Date of Patent: Apr. 28, 2026

(54) VISUAL EXAMINING AND TRAINING DEVICE

(71) Applicant: ORTHOV TECHNOLOGY COMPANY LIMITED, Kaohsiung City (TW)

(72) Inventors: Hsuan-Yu Huang, Kaohsiung City (TW); Shang-Min Yeh, Taichung City (TW); Ya-Yu Chen, Kaohsiung City (TW); Chia-Rong Lee, Kaohsiung City (TW); Chi-Hung Lee, Taichung City (TW); Chie-Tong Kuo, Kaohsiung City (TW)

(73) Assignee: ORTHOV TECHNOLOGY COMPANY LIMITED, Kaohsiung City (TW)

( * ) Notice: Subject to any disclaimer, the term of this patent is extended or adjusted under 35 U.S.C. 154(b) by 659 days.

(21) Appl. No.: 18/080,124

(22) Filed: Dec. 13, 2022

(65) Prior Publication Data

US 2023/0181411 A1 Jun. 15, 2023

(30) Foreign Application Priority Data

Dec. 14, 2021 (TW) ................................. 110146764
May 10, 2022 (TW) ................................. 111117549

(51) Int. Cl.
*A61H 5/00* (2006.01)
*A61B 3/08* (2006.01)
(52) U.S. Cl.
CPC ................ *A61H 5/00* (2013.01); *A61B 3/08* (2013.01); *A61H 2201/0192* (2013.01);
(Continued)

(58) Field of Classification Search
CPC .............. A61H 5/00; A61H 2201/0192; A61H 2201/1207; A61H 2201/1604;
(Continued)

(56) References Cited

U.S. PATENT DOCUMENTS 6,215,460 B1 * 4/2001 Mizoguchi ......... G02B 27/0172
348/E13.041

FOREIGN PATENT DOCUMENTS

CN 106983642 A * 7/2017 ............... A61H 5/00
CN 109431683 A * 3/2019 ............... A61F 9/04
(Continued)

OTHER PUBLICATIONS

Search Report appended to an Office Action, which was issued to Chinese counterpart application No. 202210914773.5 by the CNIPA on Dec. 8, 2025 with an English translation thereof.

*Primary Examiner* — William R Alexander
*Assistant Examiner* — Alaina Marie Swanson
(74) *Attorney, Agent, or Firm* — Muncy, Geissler, Olds & Lowe, P.C.

(57) ABSTRACT

A visual examining and training device includes a wearing unit that is suitable for wearing on a head of a user, that is configured to be disposed in front of the eyes of the user, and that has a main housing, and two lens adjusting units spacedly disposed in the main housing and each of which includes a lens carrier having a tubular member defining an inner space, a rotary lens holder assembly disposed in the inner space, two prisms coaxially disposed in the rotary lens holder assembly, a focal length adjusting lens disposed in the inner space spaced apart from the prisms, and a drive mechanism connected to the rotary lens holder assembly for driving the same together with the prisms to rotate. A control unit is signally connected to the drive mechanisms of the lens adjusting units for controlling operation of the same.

11 Claims, 20 Drawing Sheets

(52) U.S. Cl.
      CPC ................ *A61H 2201/1207* (2013.01); *A61H 2201/1604* (2013.01); *A61H 2201/1671* (2013.01)

(58) Field of Classification Search
      CPC ........... A61H 2201/1671; A61H 5/005; A61H 2201/14; A61H 2201/165; A61H 2201/5097; A61H 2205/024; A61B 3/08; A61B 3/04; A61B 3/02; A61B 3/0016; A61B 3/0075; A61B 3/085; A61B 3/09
      USPC ........................................................ 351/203
      See application file for complete search history.

(56)                 References Cited

FOREIGN PATENT DOCUMENTS

| GB | 2415265 | A | * | 12/2005 | ............ | G02B 30/36 |
|----|---------|---|---|---------|-------------|------------|
| JP | H08560 | A | | 1/1996 | | |
| JP | 4031313 | B2 | * | 1/2008 | | |
| JP | 2012209941 | A | | 10/2012 | | |
| KR | 20110009106 | U | | 9/2011 | | |

* cited by examiner

VISUAL EXAMINING AND TRAINING DEVICE

CROSS-REFERENCE TO RELATED APPLICATION

This application claims priority to Taiwanese Invention Patent Application No. 110146764, filed on Dec. 14, 2021, and Taiwanese Invention Patent Application No. 111117549, filed on May 10, 2022.

FIELD

The disclosure relates to a visual examining and training device of human eyes.

BACKGROUND

When reading and using digital multimedia electronic products at near distance for a long time, the ciliary muscles (intraocular muscles) of the eyes responsible for regulating the visual distance will be in a tight state, so that the spasms cannot relax which results in blurred images when looking at a distance, and the refractive state can produce more myopia than in a normal condition. The myopia caused by spasms of the ciliary muscles is called pseudomyopia.

In order to improve the aforementioned problems, currently, the industry provides an eye training device in the market, which can be worn on the head of a user and which has two training modules respectively corresponding to the eyes of the user. Each training module includes multiple lenses of different diopters, and an electric shifting mechanism that can be actuated to drive one of the lenses to displace and align with one of the eyes of the user. By way of switching to provide lenses of different diopters, the eye muscles can be forced to move in accordance with the changes in the diopters of the lenses, and can be allowed to maintain a good adjustment ability.

However, the eye training device currently provided by the industry uses spherical lenses to train and strengthen the adjustment ability of the eyes, but cannot provide training for visual symptoms induced by abnormal binocular fusion ability of the eyes. Hence, there is still room for improvement of the existing eye training device.

SUMMARY

Therefore, an object of the present disclosure is to provide a visual examining and training device that can alleviate at least one of the drawbacks of the prior art.

Accordingly, a visual examining and training device of this disclosure is suitable for wearing by a user, and includes a wearing unit, two lens adjusting units, and a control unit. The wearing unit is suitable for wearing on a head of the user, is configured to be disposed in front of the eyes of the user, and includes a main housing. The lens adjusting units are disposed in the main housing and are spaced apart from each other in a left-right direction for the eyes of the user to view an object. Each lens adjusting unit includes a lens carrier, a rotary lens holder assembly, two prisms, a focal length adjusting lens, and a drive mechanism.

The lens carrier includes a plate member formed with two through holes spaced apart in the left-right direction, a tubular member extending rearwardly from the plate member at a position corresponding to one of the through holes and defining an inner space communicating and aligned with the one of the through holes, and a support bracket connected to the plate member and the tubular member and corresponding in position to the other one of the through holes. The rotary lens holder assembly is disposed in the inner space of the tubular member. The prisms are coaxially disposed in the rotary lens holder assembly and are spaced apart from each other in a front-rear direction.

The focal length adjusting lens is disposed in the inner space of the tubular member and is spaced apart from the prisms in the front-rear direction for adjusting a focal length of a corresponding one of the eyes of the user. The drive mechanism is mounted on the support bracket and is connected to the rotary lens holder assembly for driving the rotary lens holder assembly together with the prisms to rotate. The control unit is signally connected to the drive mechanisms of the lens adjusting units, and can be triggered by a control signal to control the operation of the drive mechanisms.

BRIEF DESCRIPTION OF THE DRAWINGS

Other features and advantages of the disclosure will become apparent in the following detailed description of the embodiments with reference to the accompanying drawings. It is noted that various features may not be drawn to scale.

DETAILED DESCRIPTION

Figure 1:
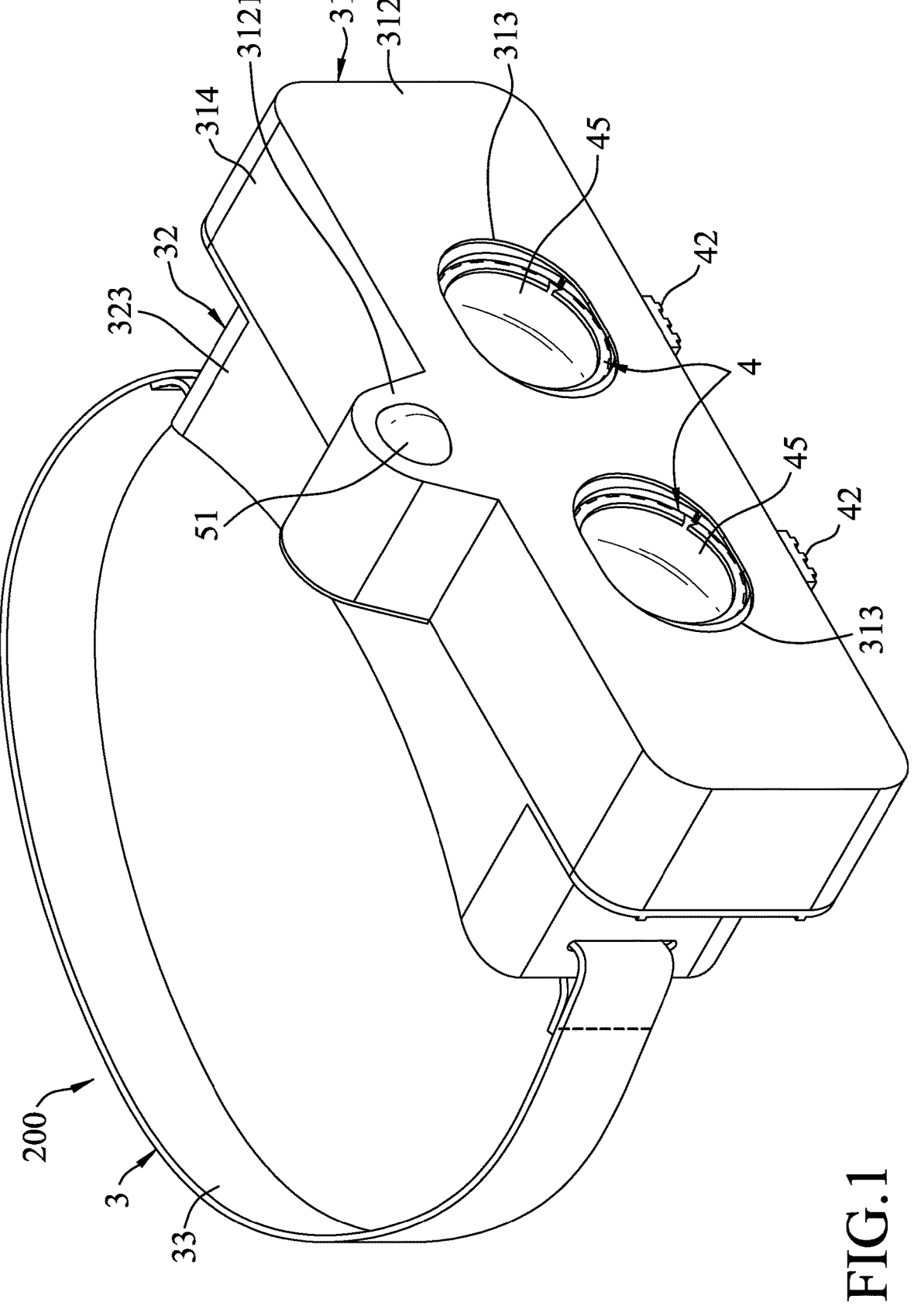
FIG. 1 is a perspective view of a visual examining and training device according to the first embodiment of the present disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
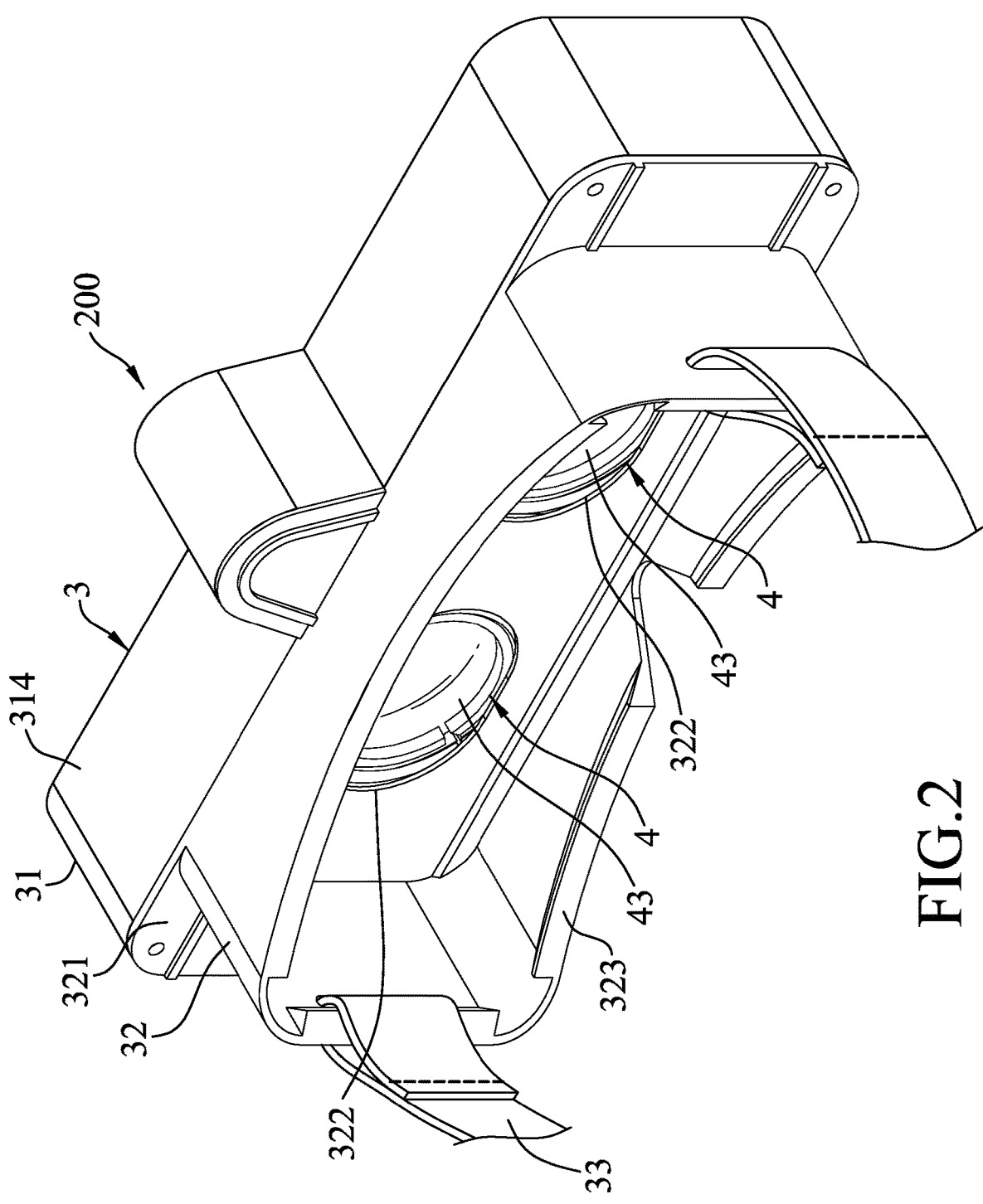
FIG. 2 is a fragmentary perspective view of the first embodiment taken from another angle.
Figure 3:
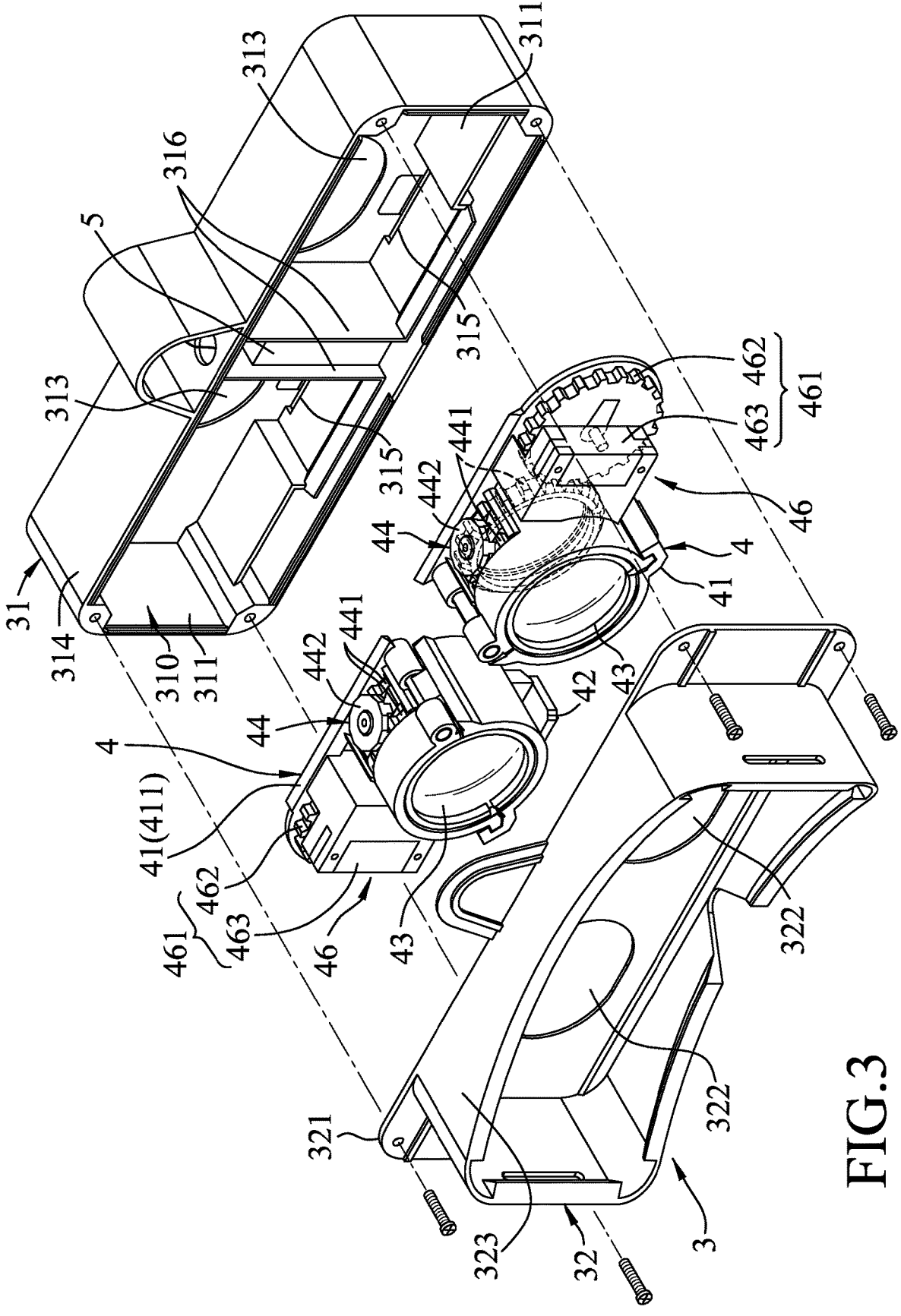
FIG. 3 is an exploded perspective view of the first embodiment, but without a strap.

Referring to FIGS. 1 to 3, a visual examining and training device 200 according to the first embodiment of the present disclosure is suitable for wearing on a head of a user, and can be used for binocular fusion ability test, muscle contraction training around the eyes of the user, and training rotation of eyeballs of the eyes of the user. Further, the visual examining and training device 200 can communicate wirelessly with an electronic device (not shown), so that it can be conveniently operated by wireless remote control of the electronic device. The electronic device may be a mobile phone, a tablet computer, a smart watch, smart glasses, and a general computer, but not limited thereto.

The visual examining and training device 200 includes a wearing unit 3, and two lens adjusting units 4 and a control unit 5 disposed on the wearing unit 3.

The wearing unit 3 is suitable for wearing on the head of the user, is configured to be disposed in front of the eyes of the user, and includes a main housing 31, an eye-covering housing 32 disposed rearwardly of the main housing 31 for covering and surrounding the eyes of the user, and a strap 33 that is elastically stretchable and deformable and that has two opposite ends connected to left and right sides of the eye-covering housing 32.

The main housing 31 includes a main front wall 312 having a substantially rectangular shape, a main surrounding wall 314 extending rearwardly from a periphery of the main front wall 312, and two support walls 316 spaced apart in a left-right direction and uprightly connected to an inner surface of the main surrounding wall 314 between upper and lower portions thereof. The main front wall 312 and the main surrounding wall 314 cooperatively define a mounting space 310 having an opening that faces rearward. The support walls 316 divide the mounting space 310 into two space sections 311 spaced apart in the left-right direction. However, in actual practice, the support walls 316 may be omitted. The main front wall 312 has two first view holes 313 extending therethrough in a front-rear direction and respectively communicating with the space sections 311. The lower portion of the main surrounding wall 314 is formed with two slots 315 that extend therethrough in a top-bottom direction at a location in proximity to a bottom edge of the main front wall 312, that extend in the left-right direction, and that respectively communicate with the space sections 311.

The eye-covering housing 32 includes an eye-covering front wall 321 that has a substantially rectangular shape and that is connected to a rear side of the main surrounding wall 314 for covering the mounting space 310, and an eye-covering surrounding wall 323 extending rearwardly from a rear side of the eye-covering front wall 321 for surrounding the eyes of the user. The eye-covering front wall 321 has two second view holes 322 extending therethrough in the front-rear direction, respectively communicating with the space sections 311, and opposite to the first view holes 313.

Figure 4:
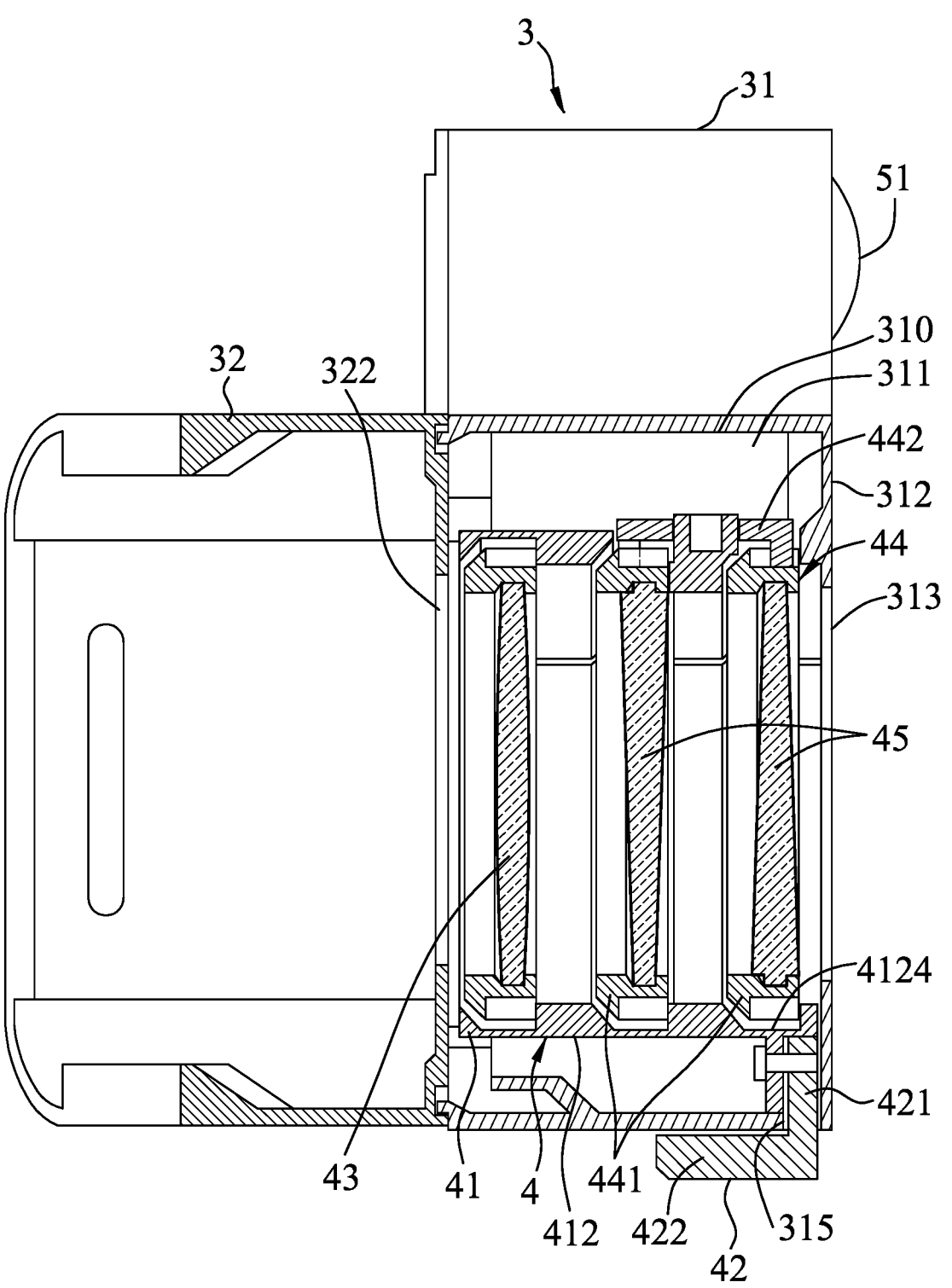
FIG. 4 is a side sectional view of the first embodiment.
Figure 5:
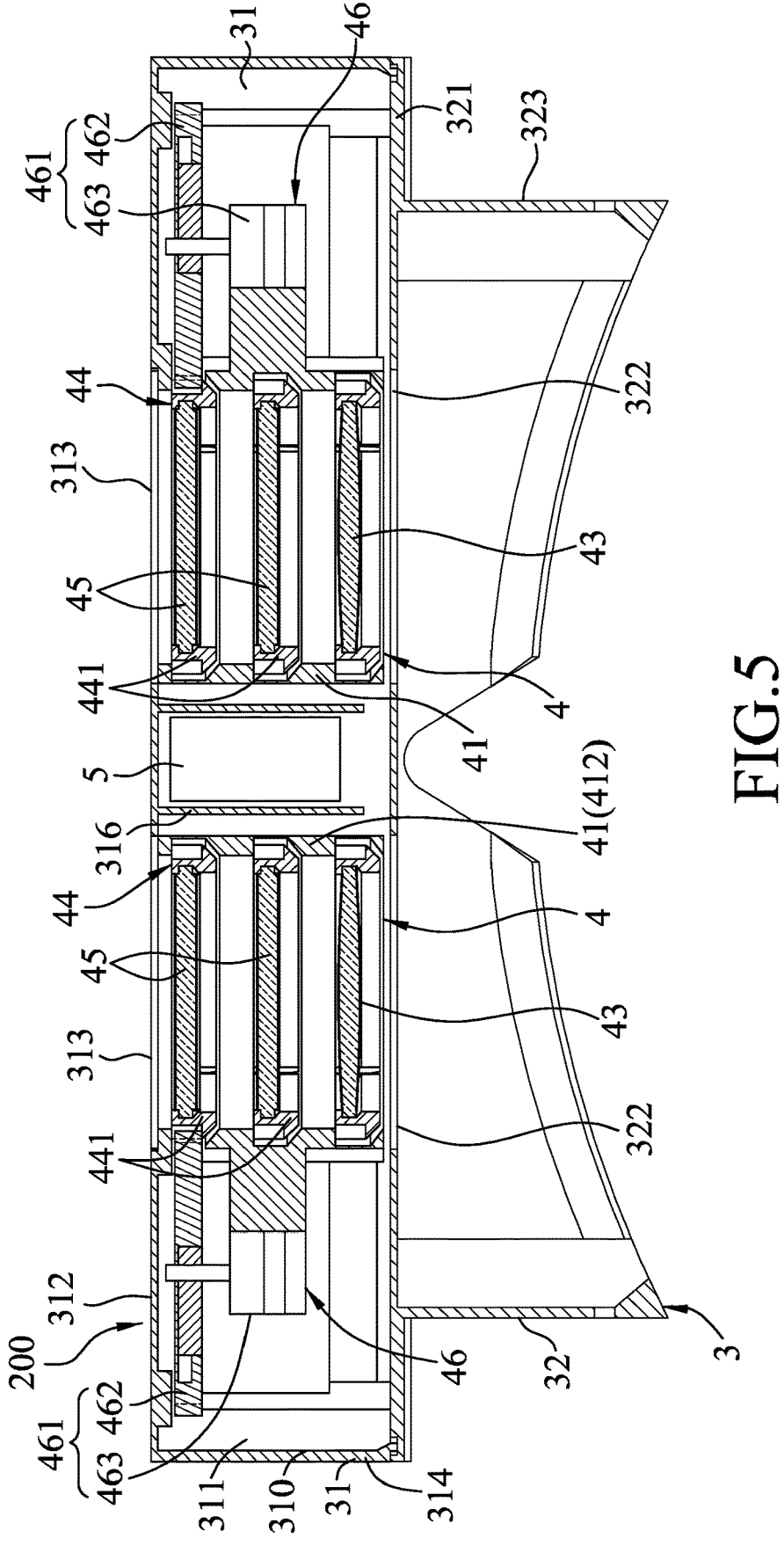
FIG. 5 is a top sectional view of the first embodiment.

Referring to FIGS. 4 and 5, in combination with FIG. 3, the lens adjusting units 4 are respectively mounted in the space sections 311, are movable within the space sections 311 in the left-right direction, and are located between the main front wall 312 and the eye-covering front wall 321. The lens adjusting units 4 are symmetrical and are mirror images of each other, only one of the lens adjusting units 4 will be described in detail hereinafter for convenience of description (??).

Figure 6:
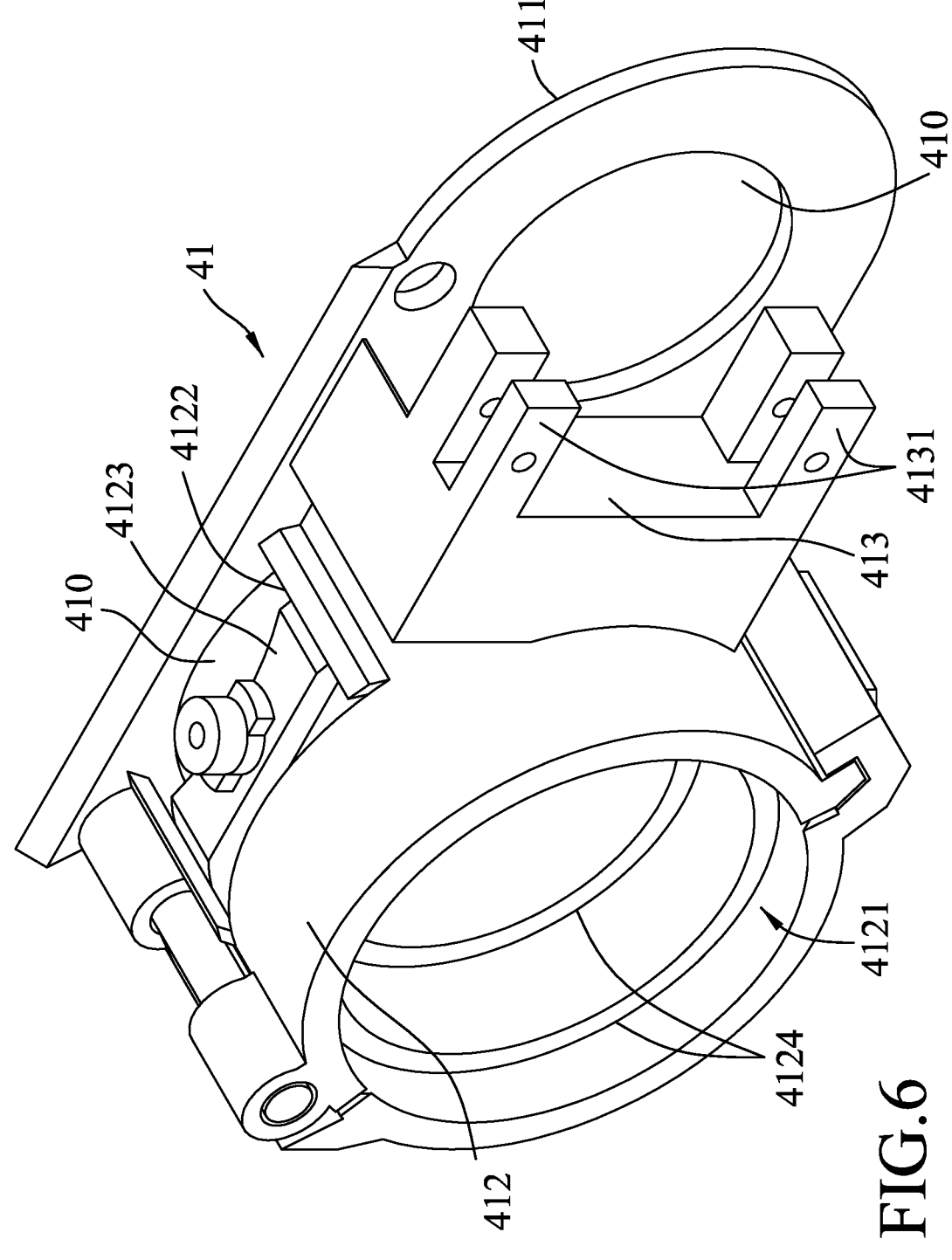
FIG. 6 is a perspective view of a lens carrier of the first embodiment.

Each lens adjusting unit 4 includes a lens carrier 41, an adjusting member 42, a focal length adjusting lens 43, a rotary lens holder assembly 44, two prisms 45 and a drive mechanism 46. The lens carrier 41 is disposed in and movable along a corresponding one of the space sections 311 in the left-right direction, and, as shown in FIG. 6, includes a plate member 411 formed with two through holes 410 spaced apart in the left-right direction, a tubular member 412, and a support bracket 413. The tubular member 412 extends rearwardly from the plate member 411 at a position corresponding to one of the through holes 410, and defines an inner space 4121 communicating and aligned with the one of the through holes 410. In this embodiment, the tubular member 412 has three annular grooves 4124 (see FIGS. 4 and 6) indented inwardly from an inner surface thereof, communicating with the inner space 4121, and spaced apart in the front-rear direction. An upper portion of the tubular member 412 is formed with a cutout portion 4122 communicating with the inner space 4121, and a mounting seat 4123 extending across the cutout portion 4122. The support bracket 413 is connected to the plate member 411 and the tubular member 412, and includes two support arms 4131 facing in a direction opposite to the tubular member 412 and corresponding in position to the other through hole 410.

Figure 7:
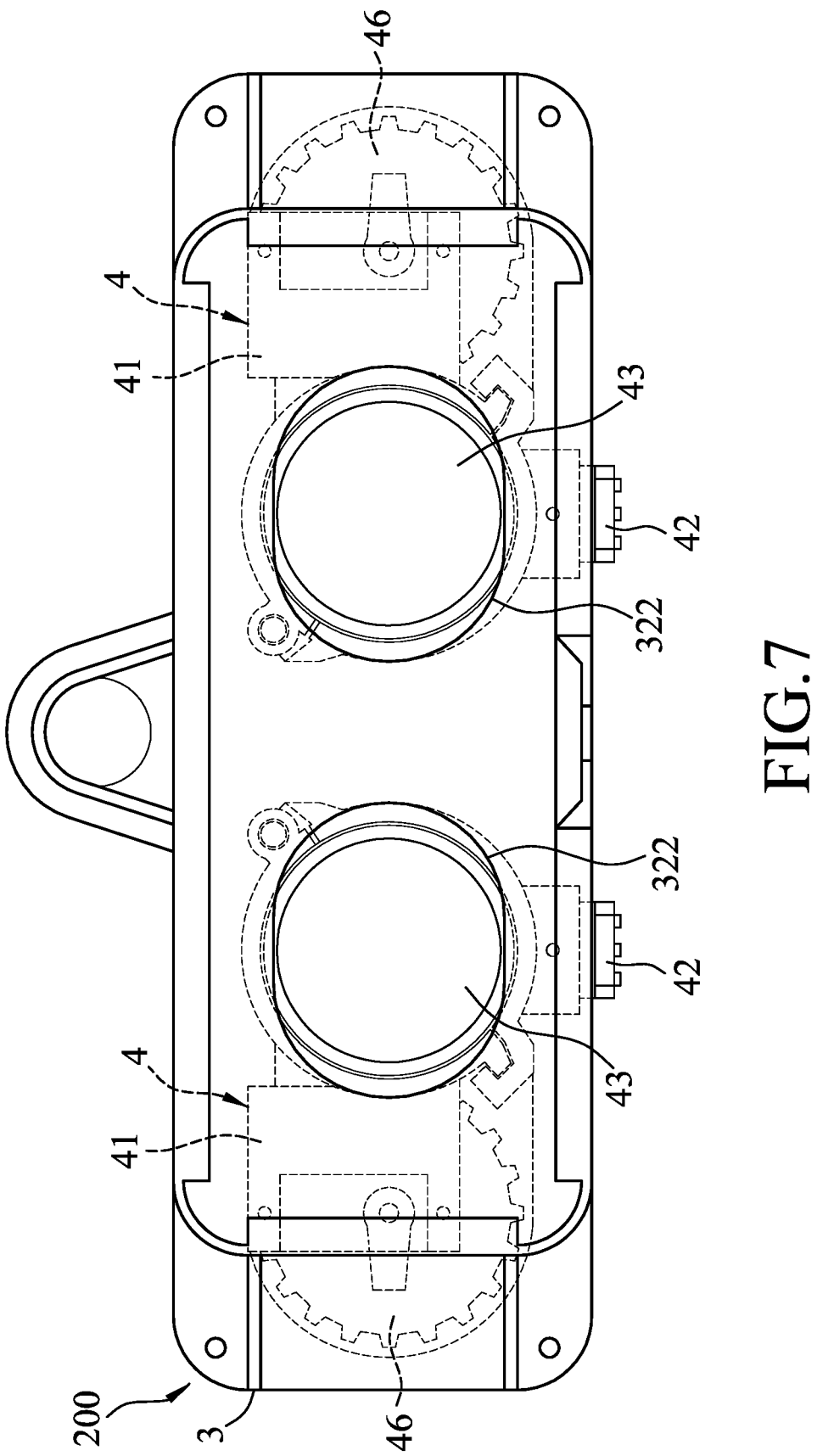
FIG. 7 is a rear side view of the first embodiment.
Figure 8:
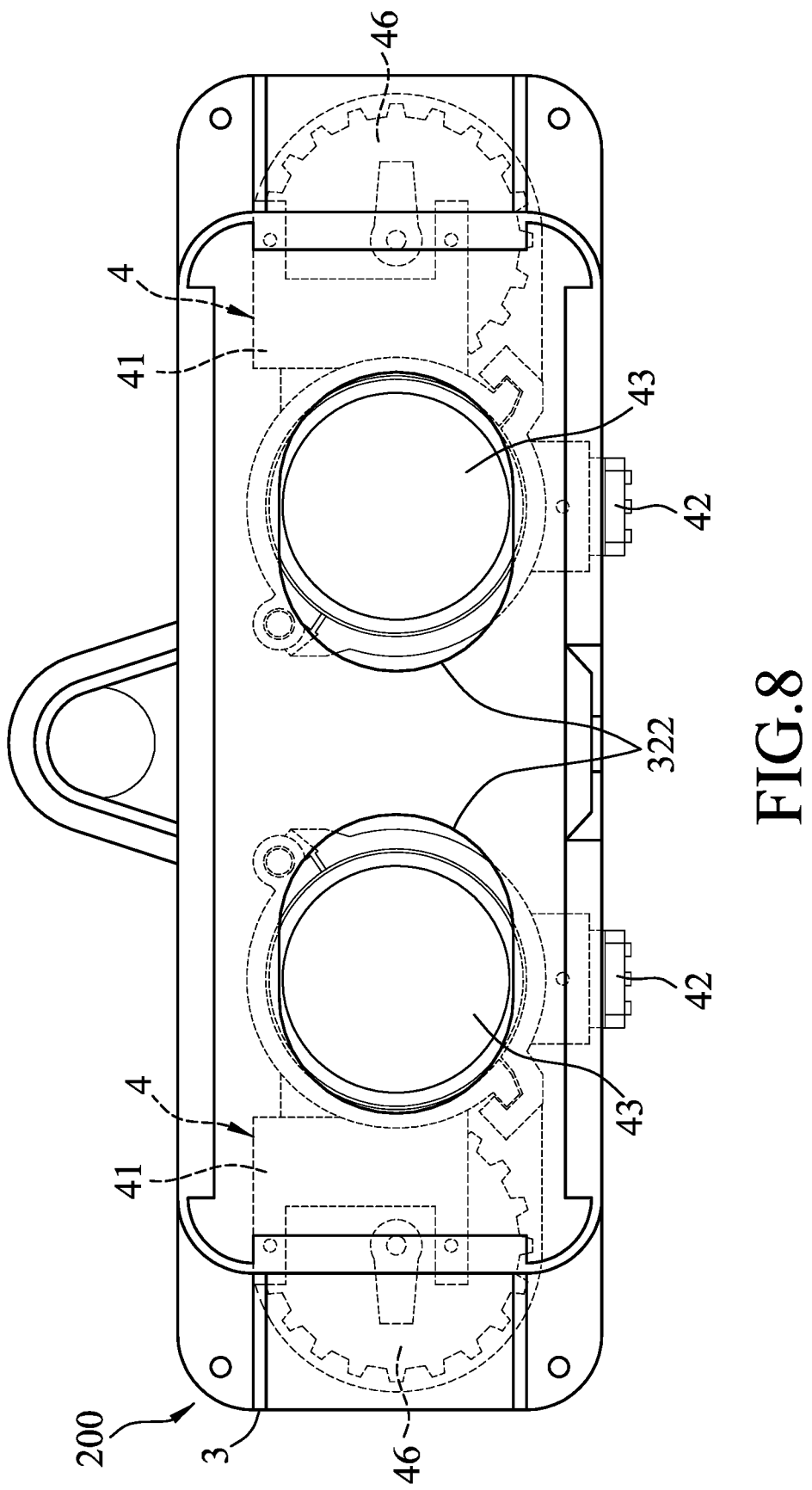
FIG. 8 is a view similar to FIG. 7, but with two lens adjusting units being opposite to each other in a left-right direction after being shifted relative to a wearing unit.

Referring to FIGS. 7 and 8, in combination with FIG. 4, the adjusting member 42 has a protruding portion 421 and an operating portion 422. The protruding portion 421 extends from a bottom side of the tubular member 412 in proximity to the plate member 411 and out of a corresponding one of the slots 315. The operating portion 422 extends horizontally and rearwardly from a bottom end of the protruding portion 421, and is located immediately below the lower portion of the main surrounding wall 314. The operating portion 422 is operable to move the protruding portion 421 along the corresponding slot 315 in the left-right direction.

The focal length adjusting lens 43 is disposed in one of the annular grooves 4124 of the tubular member 412 that is proximate to a rear end thereof, and is located between one of the first view holes 313 and a corresponding one of the second view holes 322. The focal length adjusting lens 43 can be used for adjusting a focal length of a corresponding one of the eyes of the user to a predetermined distance in front of the corresponding eye. In this embodiment, the focal length adjusting lens 43 is a convex lens. For people with normal vision, when the focal length adjusting lens 43 is a +2.5D convex lens, the focal length can be adjusted to a distance of about 40 cm in front of the eye; and, when the focal length adjusting lens 43 is a +3.3D convex lens, the focal length can be adjusted to a distance of about 30 cm in front of the eye.

With reference to FIGS. 3 to 5, the rotary lens holder assembly 44 is disposed in the inner space 4121 of the tubular member 412 and is located forwardly of the focal length adjusting lens 43. The rotary lens holder assembly 44 includes two rotary lens holders 441 and a transmission gear 442. The rotary lens holders 441 are disposed rotatably and coaxially in the inner space 4121 of the tubular member 412.

Specifically, the rotary lens holders 441 are respectively disposed in the other two of the annular grooves 4124 of the tubular member 412, and are located at positions corresponding to front and rear sides of the mounting seat 4123. Each rotary lens holder 441 is substantially circular, and has an outer peripheral surface provided with a plurality of spaced-apart teeth. The transmission gear 442 is rotatably mounted on the mounting seat 4123, and meshes with the teeth of the rotary lens holders 441. The rotary lens holders 441 can be driven by the transmission gear 442 to synchronously rotate in opposite directions.

Figure 9:
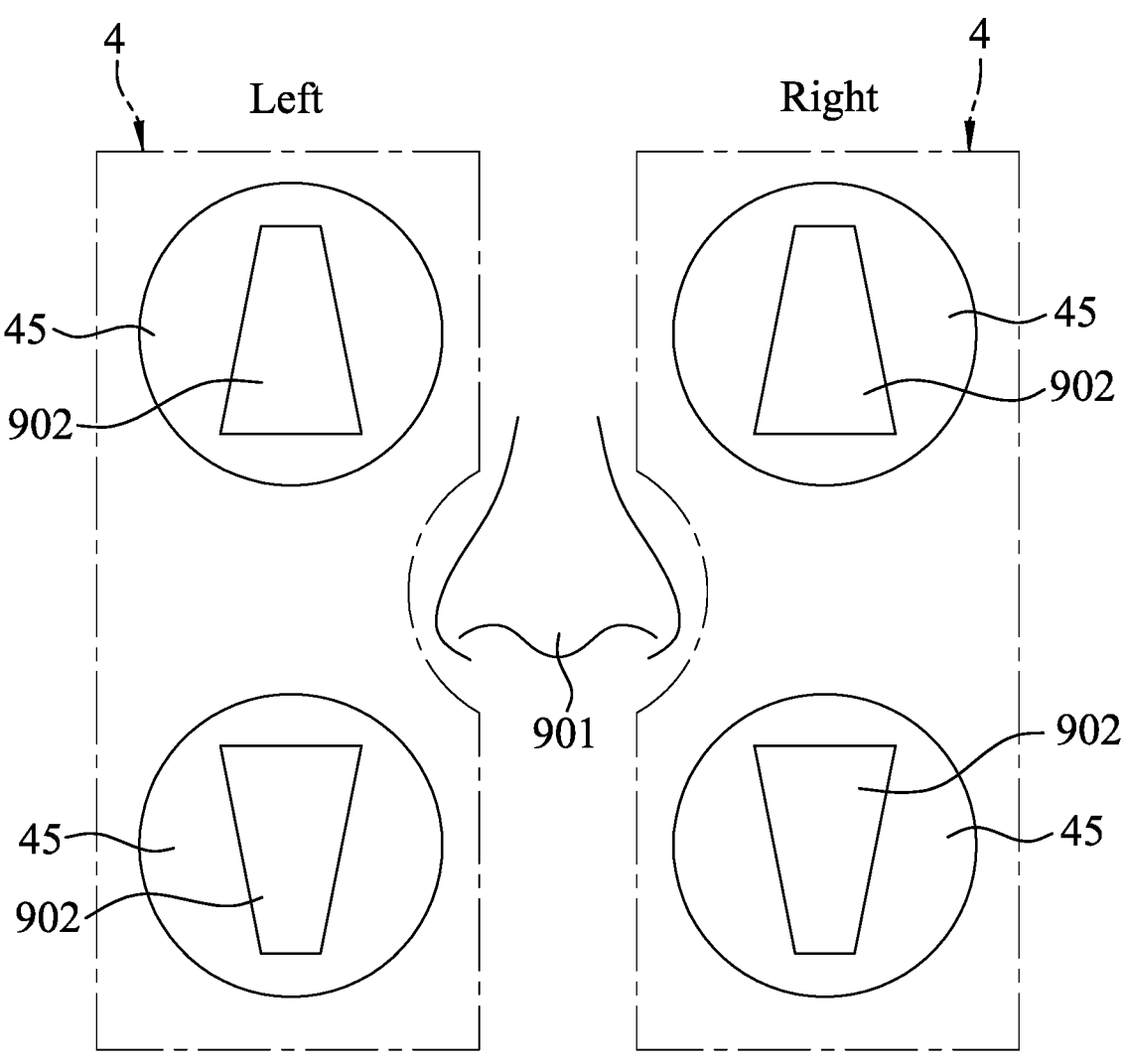
FIG. 9 is a schematic view of the first embodiment, illustrating two prisms of each lens adjusting unit located at a zero prism diopter state.
Figure 10:
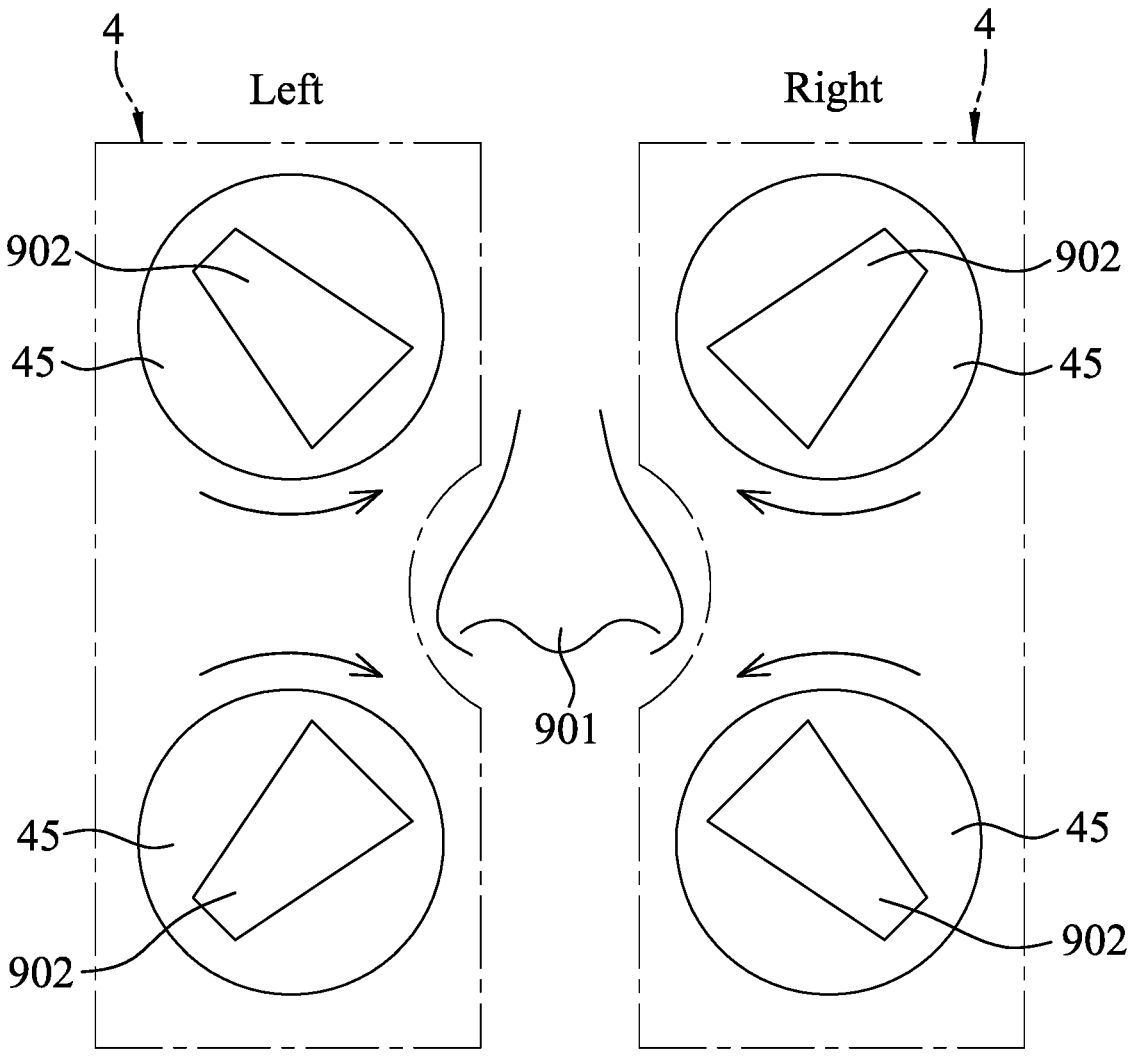
FIG. 10 is a view similar to FIG. 9, but illustrating relative positions of the prisms of the lens adjusting units when rotated to a base in (BI) state.
Figure 11:
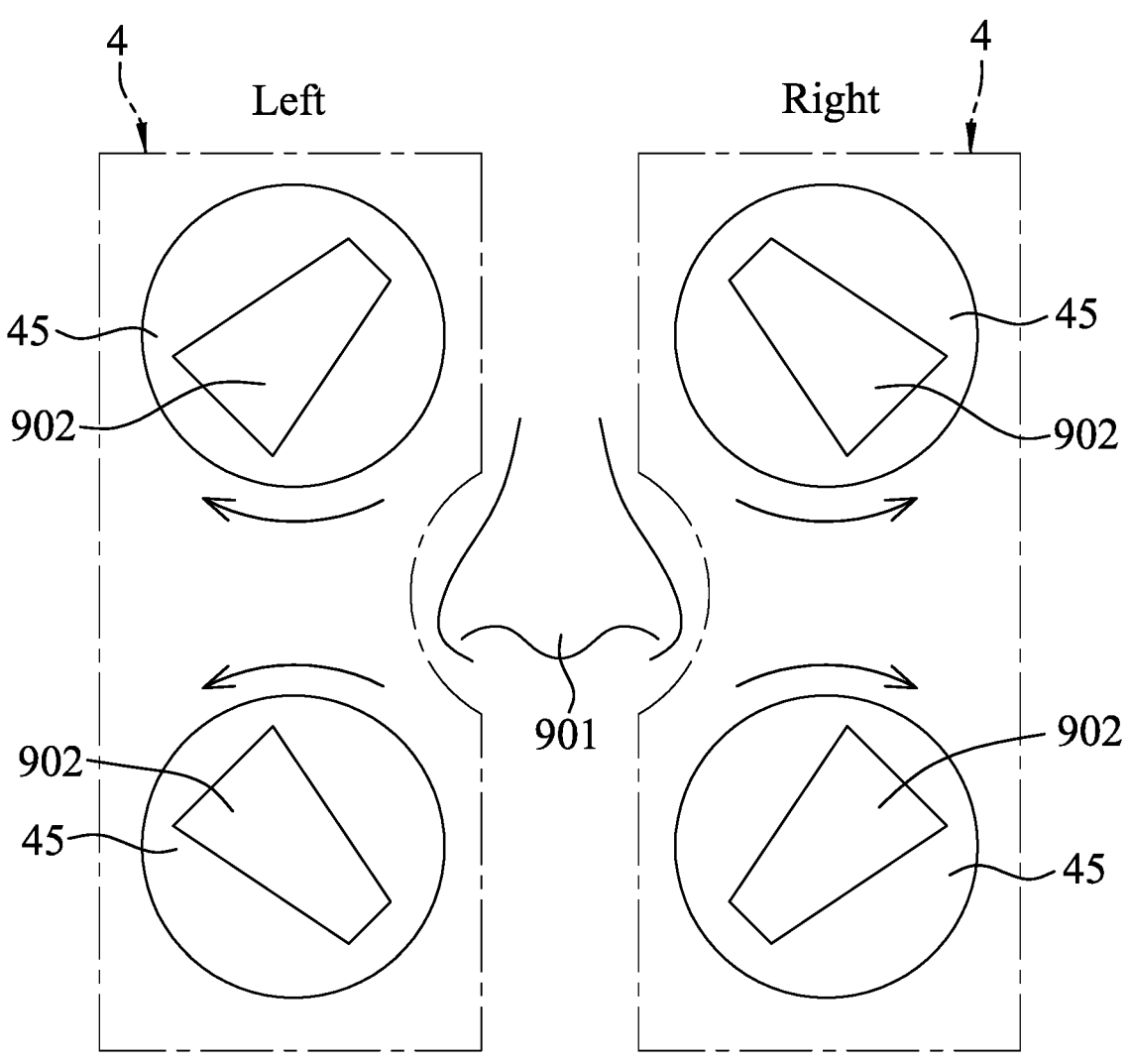
FIG. 11 is a view similar to FIG. 9, but illustrating relative positions of the prisms of the lens adjusting units when rotated to a base out (BO) state.

The prisms 45 are received respectively and fixedly in the rotary lens holders 441. In this embodiment, the prisms 45 are vertical prisms of same diopters, but the bases thereof are oppositely disposed (see FIG. 9). For the convenience of description, in FIGS. 9 to 11, a trapezoidal pattern 902 is marked in each prism 45 to schematically represent the thickness distribution thereof, and a bottom side of the trapezoidal pattern 902 corresponds to the base of the prism 45. The prisms 45 can be driven by the respective rotary lens holders 441 to rotate therewith in opposite directions and to cooperatively produce a base in (BI) (see FIG. 10) or a base out (BO) (see FIG. 11) horizontal prism power. The focal length adjusting lens 43 is located rearwardly of the prisms 45 (see FIG. 4).

The drive mechanism 46 includes a drive module 461 mounted on the lens carrier 41. The drive module 461 includes a motor assembly 463 fixed to the support arms 4131 of the support bracket 413, and a drive gear 462 journalled on a shaft of the motor assembly 463 and meshing with the teeth of one of the rotary lens holders 441. The motor assembly 46 is signally connected to the control unit 5, and can be controlled by the control unit 5 to operate and drive the drive gear 462 to rotate the one of the rotary lens holders 441 relative to the lens carrier 41. The driven one of the rotary lens holders 441 will, in turn, drive the other rotary lens holder 441 to rotate in opposite direction through the transmission gear 442. The prisms 45 are respectively driven by the rotary lens holders 441 to rotate therewith in opposite directions.

In this embodiment, the drive mechanism 46 uses the drive module 461 to drive one of the rotary lens holders 441 to rotate, which in turn, drives the other rotary lens holder 441 to rotate in opposite direction through the transmission gear 442. However, in other embodiments, the drive module 461 may be directly connected to the transmission gear 442 and directly drive rotation of the same, so that the transmission gear 442 can, in turn, drive the rotary lens holders 441 to synchronously rotate in opposite directions. Furthermore, because there are many ways in which the drive mechanism 46 can synchronously drive rotation of the rotary lens holders 441, the connection relationship between the drive module 461 of the drive mechanism 46 and the rotary lens holder assembly 44 is not limited to the above disclosure.

It should be noted herein that the adjusting member 42 can be operated to move left and right along the corresponding slot 315 so as to synchronously drive the lens carrier 41 to move the focal length adjusting lens 43, the rotary lens holder assembly 44, the prisms 45 and the drive mechanism 46 within the corresponding space section 311 in the left-right direction.

The control unit 5 is disposed between the support walls 316 of the main housing 31 (see FIG. 3), and is signally connected to an electronic device through a wireless communication technology. The control unit 5 can be triggered by a control signal of the electronic device to control the operations of the drive modules 461 of the drive mechanisms 46 of the lens adjusting units 4. By driving the rotary lens holders 441 of the rotary lens holder assembly 44 to rotate the prisms 45 therewith in opposite directions, the prisms 45 can be adjusted from a zero prism diopter state shown in FIG. 9 to a base in (BI) state shown in FIG. 10, in which the bases of the prisms 45 face inward, that is, the bases of the prisms 45 face the nose 901 of the user; or, a base out (BO) state shown in FIG. 11, in which the bases of the prisms 45 face outward, that is, the bases of the prisms 45 face away from the nose 901 of the user. Hence, the prisms 45 cooperatively produce a base in (BI) or a base out (BO) horizontal prism power, for example, 10BI, 20BI, 10BO, 20BO, etc. Moreover, the control unit 5 has a power switch 51 exposed from a front side of an upper extension 3121 of the main front wall 312 of the main housing 31, as shown in FIG. 1.

When the visual examining and training device 200 is worn by the user for eye testing or training, through the disposition of the focal length adjusting lenses 43 of the lens adjusting units 4, the user is allowed to relax and focus on an object at a predetermined distance in front of the eyes thereof without deliberately adjusting the muscles around the eyes, for example, relax and focus on a book that is 40 cm in front of the eyes. Furthermore, the focal length adjusting lenses 43 and the prisms 45 of the lens adjusting units 4 can align with the eyes of the user by operating the adjusting members 42 of the lens adjusting units 4 to move in the left-right direction.

Afterwards, the visual examining and training device 200 is remotely controlled through the electronic device to perform adjustment of the horizontal prism power of the prisms 45, forcing the user to turn the eyeballs in order to achieve the purpose of seeing objects clearly, so that images seen by the eyes are fused into one. Thus, the purpose of testing the binocular fusion ability of the eyes and training the muscles around the eyes to contract can be achieved.

Taking a training mode as an example, the lens adjusting units 4 can be controlled to cooperatively produce a periodic change in prism power, for example, sequentially producing 0 prism power, 10BI for 3 seconds, 0 prism power for 3 seconds, 10BO for 3 seconds, and 0 prism power for 3 seconds. Through this, the eyeballs of the eyes of the user can be trained to repeatedly rotate inward and outward. During implementation, the change mode, the change amount, and the change order of the prism power cooperatively produced by the prisms 45 can be correspondingly adjusted according to the training requirements of the user.

Taking a reading mode as an example, the lens adjusting units 4 can be made to generate a specific BI prism power, allowing the user to read with the specific BI prism power. The BI prism power can be, but not limited to, 4BI, 6BI or 8BI, so as to make the eyes of the user turn outward and maintain the adjusted BI prism power until the end of the reading.

Taking a positive and negative fusion ability test of the eyes of the user as an example, the prisms 45 of the lens adjusting units 4 are first controlled to move to the BI state, for example, gradually increasing the BI prism power at a speed of 2BI per second. In the process of gradually increasing the BI prism power, the fusion ability of the eyes of the user will gradually reach a limit, so that the image of the object being viewed will gradually become blurred, and then progresses to a breaking point where one object image is changed to two object images. Next, the prisms 45 are adjusted to move in a reverse direction at the same speed to the 0 prism diopter state, and the BI prism power when the user clearly sees the image of the single object is recorded to obtain a recovery point. After the fusion ability test of the BI prism power is completed, the prisms 45 are controlled to move to the BO state according to the above-mentioned testing method, after which the blurred point, the breaking point and the recovery point are recorded, thereby carrying out the BO prism power fusion ability test. Therefore, the visual examining and training device 200 of this disclosure can also be used for testing the binocular fusion ability of the eyes of the user.

In addition, in other embodiments, the prisms 45 of the lens adjusting units 4 may be changed to horizontal prisms 45 with the bases thereof oppositely disposed in the left-right direction, so that the prisms 45 may be rotated to cooperatively generate a base down (BD) or a base up (BU) vertical prism power, and can be used for training and testing the fusion ability of the eyes of the user in the top-bottom direction.

In the first embodiment, the purpose of providing the focal length adjusting lenses 43 in the lens adjusting units 4 is to allow the eyes of the user to relax and focus on an object at a specific distance in front thereof, and perform the rotation training of the inward and outward rotation of the eyeballs, thereby achieving the purpose of training the muscles around the eyes of the user. However, in other embodiments, the focal length adjusting lens 43 of each lens adjusting unit 4 may be a 0-degree lens or may not be provided, and the purpose of testing the fusion ability and the training of the muscles around the eyes of the user may be similarly achieved. Furthermore, the focal length adjusting lens 43 of each lens adjusting unit 4 may also be disposed in front of the prisms 45.

Figure 12:
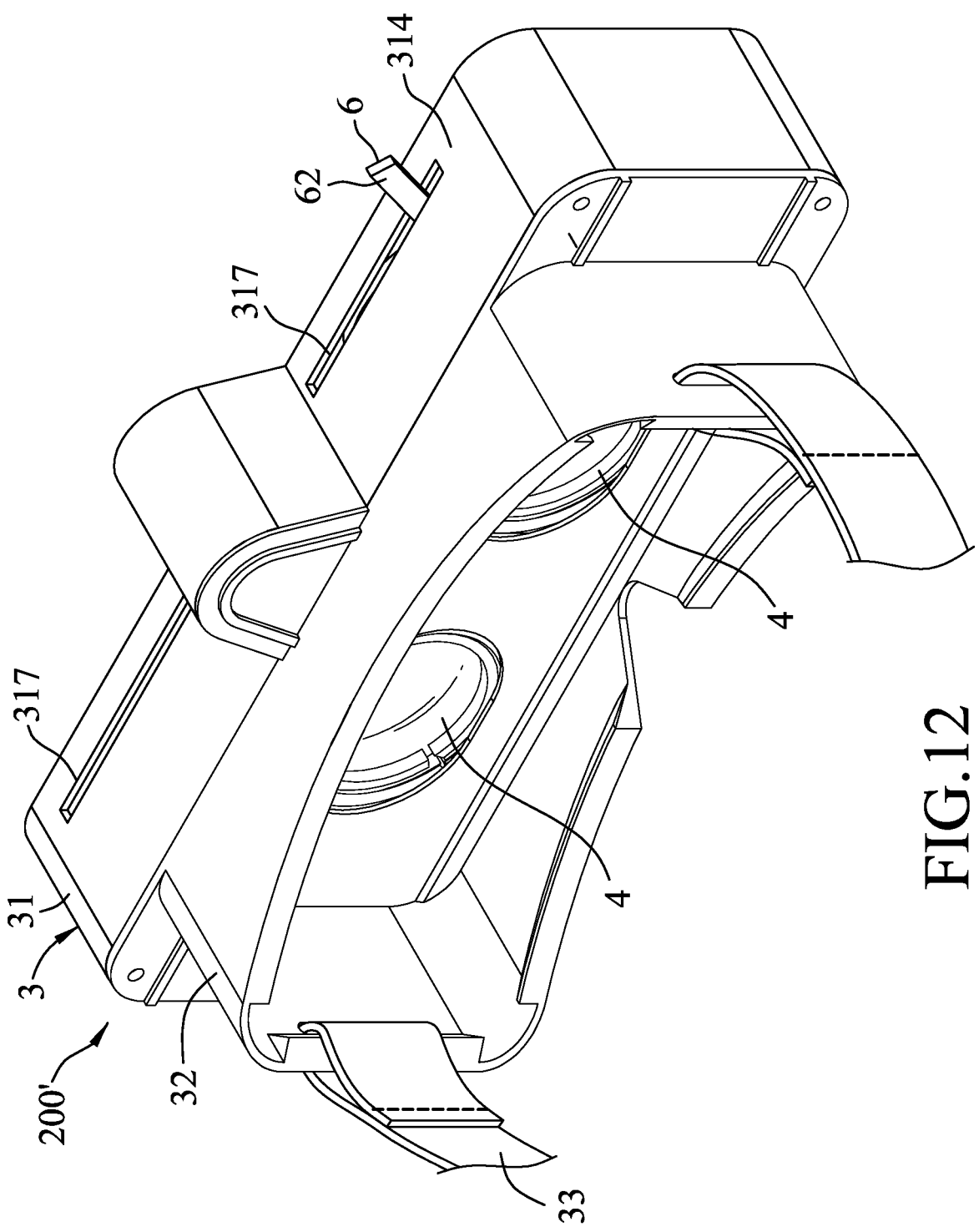
FIG. 12 is a fragmentary perspective view of a visual examining and training device according to the second embodiment of the present disclosure.
Figure 13:
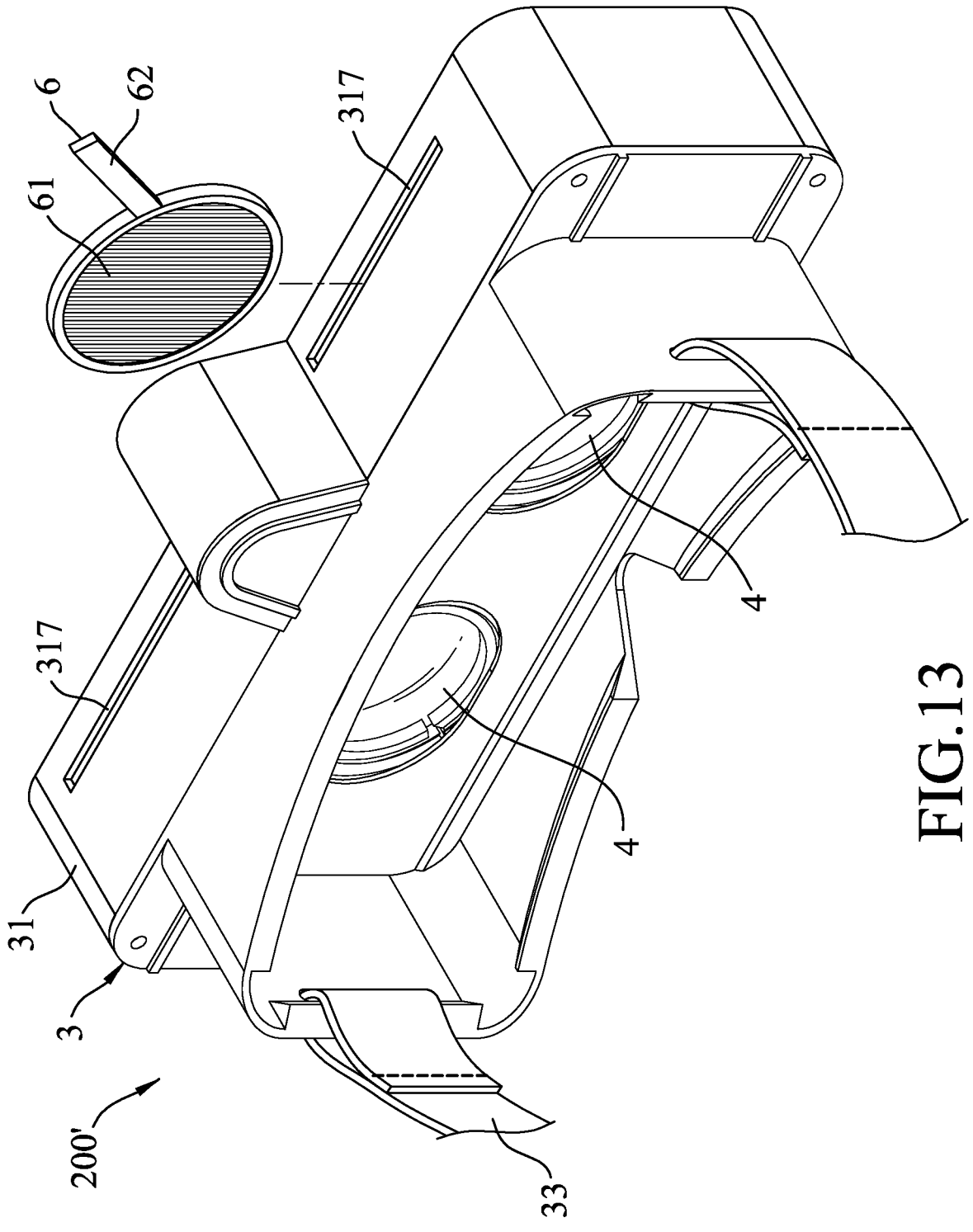
FIG. 13 is a view similar to FIG. 12, but with a Maddox rod being removed from an insertion hole of a wearing unit.
Figure 14:
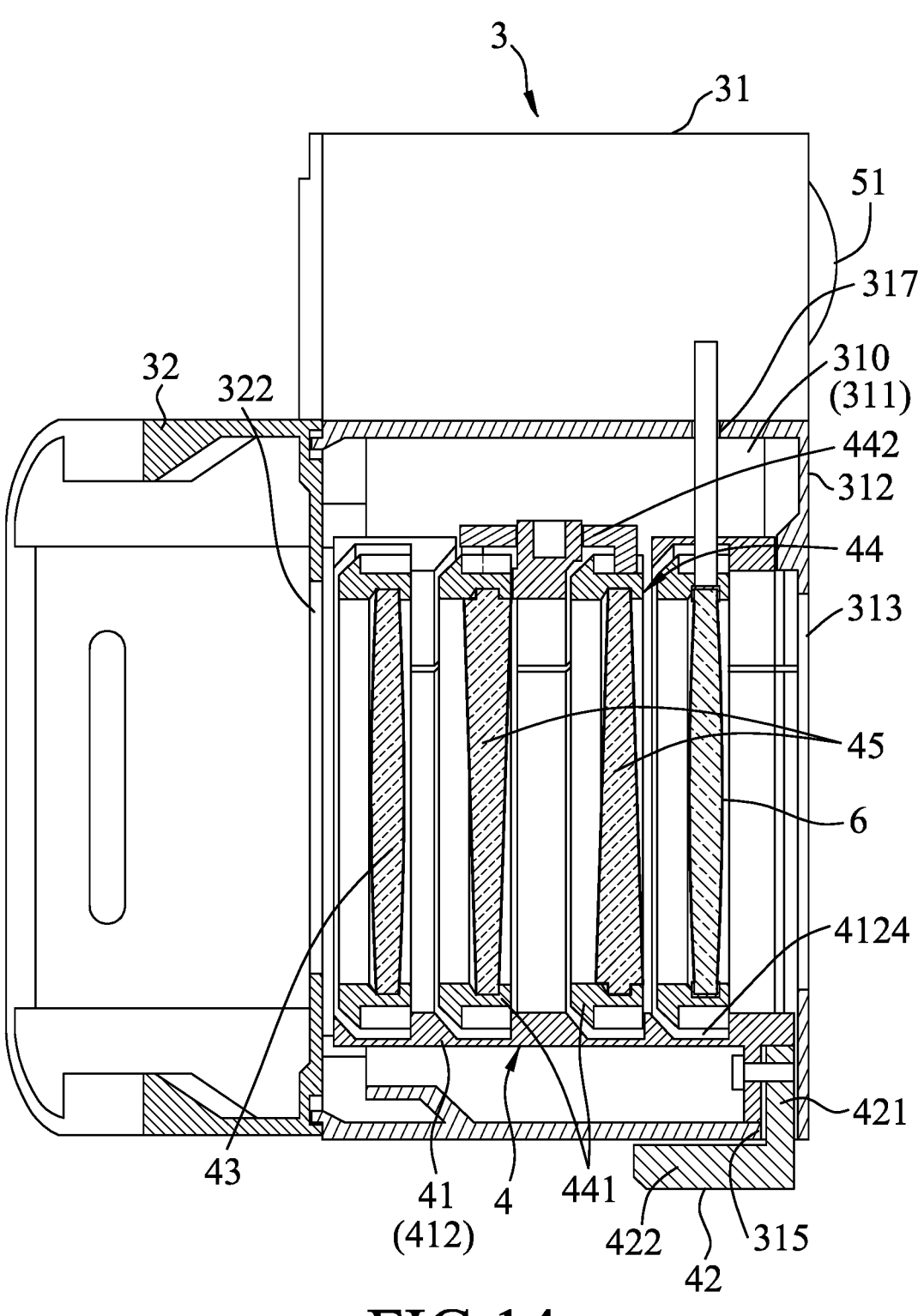
FIG. 14 is a side sectional view of the second embodiment.

Referring to FIGS. 12 to 14, a visual examining and training device 200' according to the second embodiment of the present disclosure is shown to be identical to the first embodiment, but differs in that, in the second embodiment, the tubular member 412 of the lens carrier 41 of each lens adjusting unit 4 has four spaced-apart annular grooves 4124 indented inwardly from the inner surface thereof, and the visual examining and training device 200' further comprises a Maddox rod 6 removably disposed in the wearing unit 3. Specifically, an upper portion of the main surrounding wall 314 of the main housing 31 of the wearing unit 3 is provided with two insertion holes 317 that are located in proximity to the main front wall 312 of the main housing 31, that are spaced apart in the left-right direction, that respectively communicate with the space sections 311 (see FIG. 3) of the main housing 31, and that respectively communicate with the inner spaces 4121 of the tubular members 412 of the lens carriers 41 of the lens adjusting units 4.

The focal length adjusting lens 43 is disposed in a first one of the annular grooves 4124 of the tubular member 412 that is proximate to a rear end thereof, and the rotary lens holders 441 of the rotary lens holder assembly 44 are respectively disposed in second and third ones of the annular grooves 4124 that are adjacent to each other. Each insertion hole 317 is aligned with a fourth one of the annular grooves 4124 of the tubular member 412 of the lens carrier 41 of a corresponding one of the lens adjusting units 4. The fourth annular groove 4124 is proximate to the main front wall 312.

The Maddox rod 6 is selectively inserted through one of the insertion holes 317, and is positioned in the fourth annular groove 4124 of the tubular member 412 of the lens carrier 41 of the corresponding lens adjusting unit 4. Specifically, the Maddox rod 6 is located in front of the prisms 45 of the corresponding lens adjusting unit 4. The Maddox rod 6 has a lens body 61 extending through the selected insertion hole 317 and positioned in the fourth annular groove 4124, and an operating rod body 62 extending radially outward from the lens body 61 and partially exposed from the selected insertion hole 317. When the Maddox rod 6 is inserted and positioned in the wearing unit 3, the lens body 61 thereof is coaxial with the prisms 45 of the corresponding lens adjusting unit 4. Since the Maddox rod 6 is known in the art, the structure and function thereof will not be described in detail herein.

Figure 15:
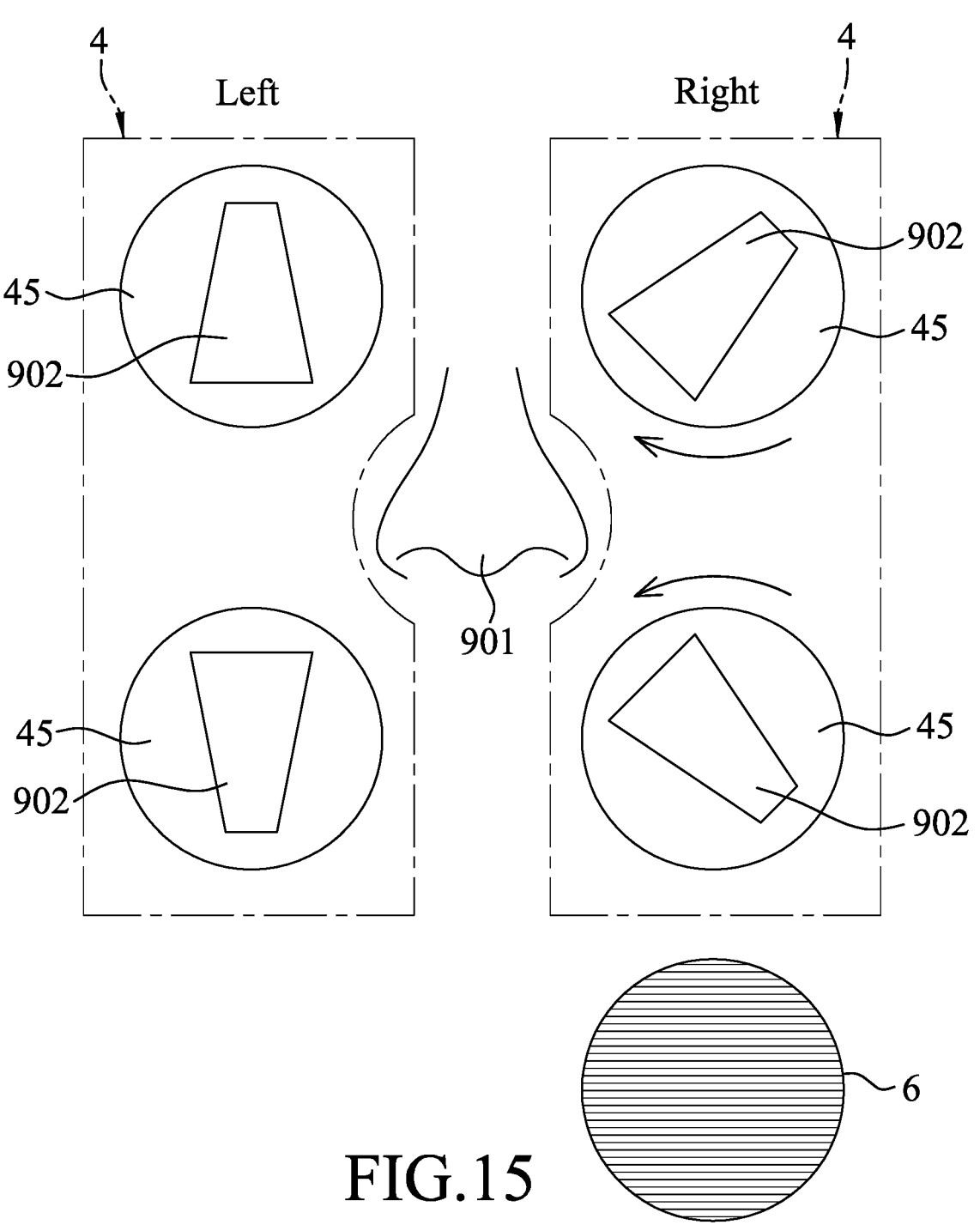
FIG. 15 is a top sectional view of the second embodiment.
Figure 16:
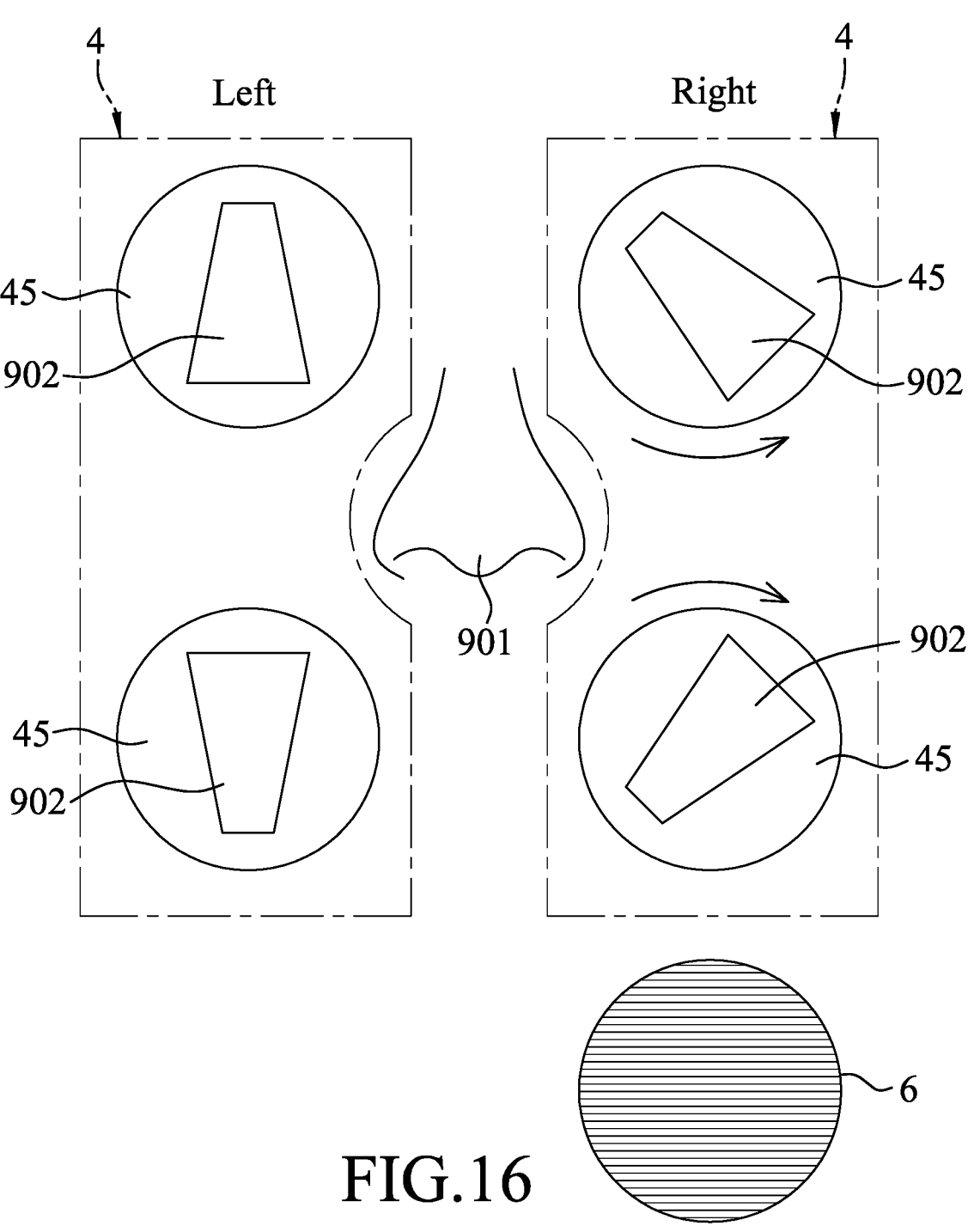
FIG. 16 is a schematic view of the second embodiment, illustrating two prisms of a left lens adjusting unit located at zero prism diopter state, while two prisms of a right lens adjusting unit located at a base in (BI) state.

Referring to FIGS. 15 and 16, in combination with FIG. 14, the second embodiment can be worn on the head of the user for carrying out a horizontal phoria test and a strabismus test. To perform the horizontal phoria test, the Maddox rod 6 is inserted, for example, into the insertion hole 317 at the right side of the wearing unit 3, so that the lens body 61 thereof is located in front of the right eye of the user, and projects a point-shaped vision mark (not shown) toward the user. Afterwards, the rotary lens holders 441 of the rotary lens holder assembly 44 of the lens adjusting unit 4 located at the right side of the wearing unit 3 are driven to rotate by the drive mechanism 46 so as to adjust the BI prism power (see FIG. 15) or the BO prism power (see FIG. 16) of the prisms 45 for detecting whether the right eye of the user has symptoms of exophoria or esophoria. If the strabismus test is to be performed, a cover test can be used in combination with the second embodiment to measure the degree of strabismus of one of the eyes of the user. Since the cover test is an existing visual detection technology, a detailed description thereof will be omitted herein.

Figure 17:
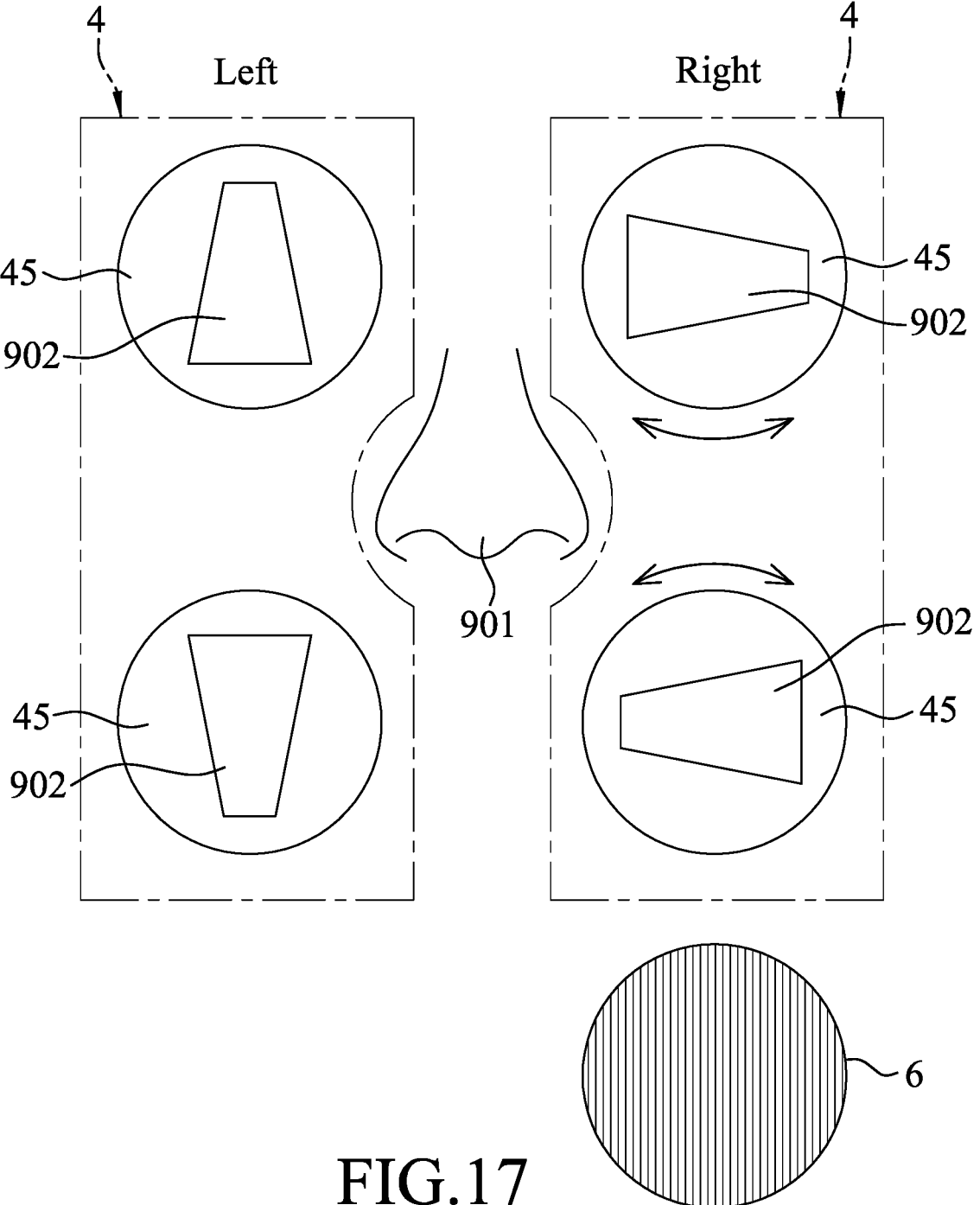
FIG. 17 is a view similar to FIG. 16, but with the two prisms of the right lens adjusting unit located at a base out (BO) state.

In other implementations of this embodiment, the lens adjusting unit 4, which is expected to receive the Maddox rod 6, may have the bases of the prisms 45 thereof disposed oppositely in the left-right direction (see FIG. 17), and may be used for adjusting the BU prism power and the BD prism power. In this case, the disclosure can be used to detect symptoms of vertical phoria. In use, the Maddox rod 6 is similarly inserted through, for example, the insertion hole 317 at the right side of the wearing unit 3 and is positioned in the fourth annular groove 4124 of the tubular member 412 of the lens carrier 41 of the corresponding lens adjusting unit 4, after which the rotary lens holders 441 of the rotary lens holder assembly 44 of the lens adjusting unit 4 located at the right side of the wearing unit 3 are driven to rotate by the drive mechanism 46 so as to adjust the BU prism power or the BD prism power of the prisms 45 for detecting whether the right eye of the user has symptoms of vertical phoria.

Figure 18:
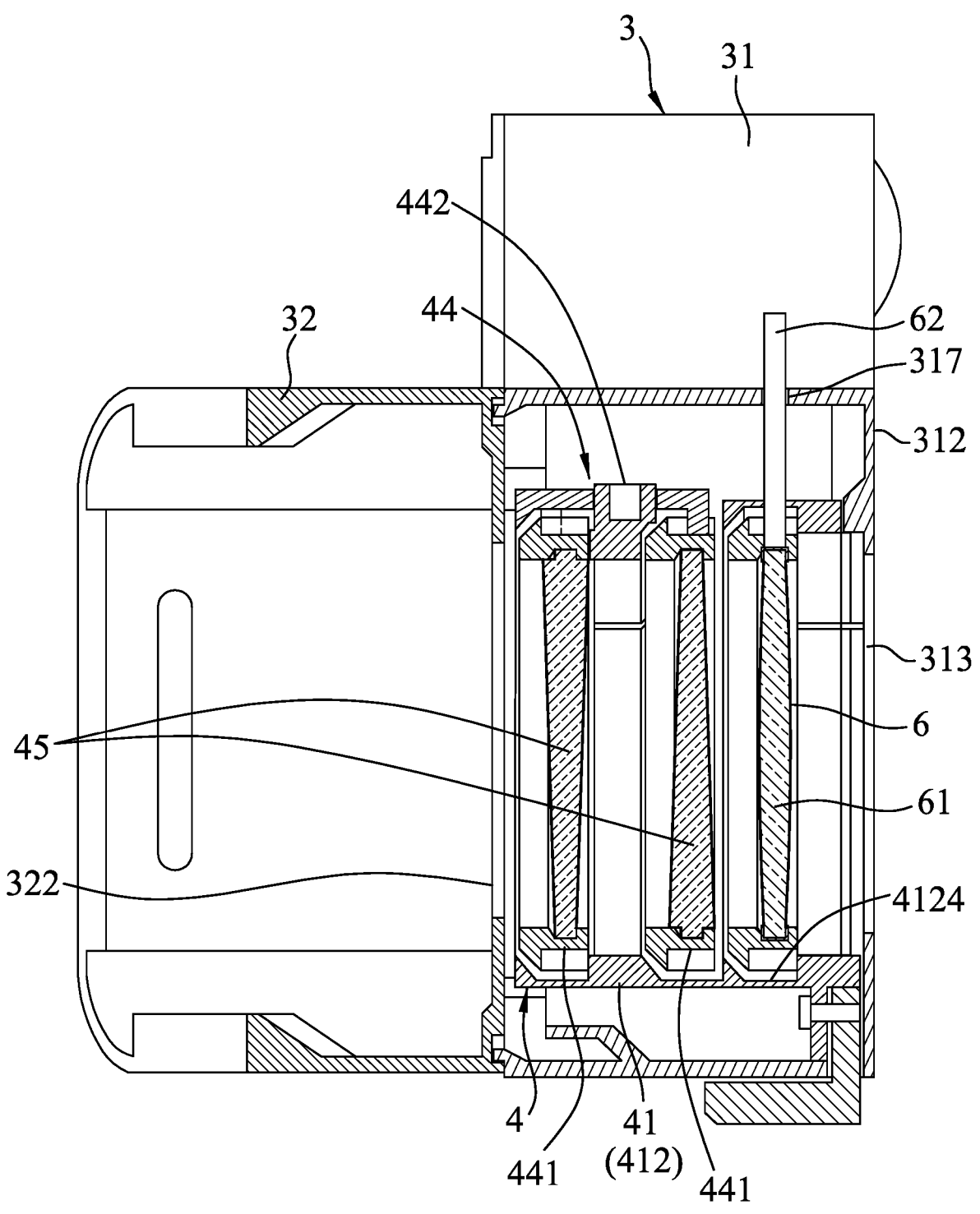
FIG. 18 is a view similar to FIG. 16, but with bases of the two prisms of the right lens adjusting unit being opposite to each other in a left-right direction.
Figure 19:
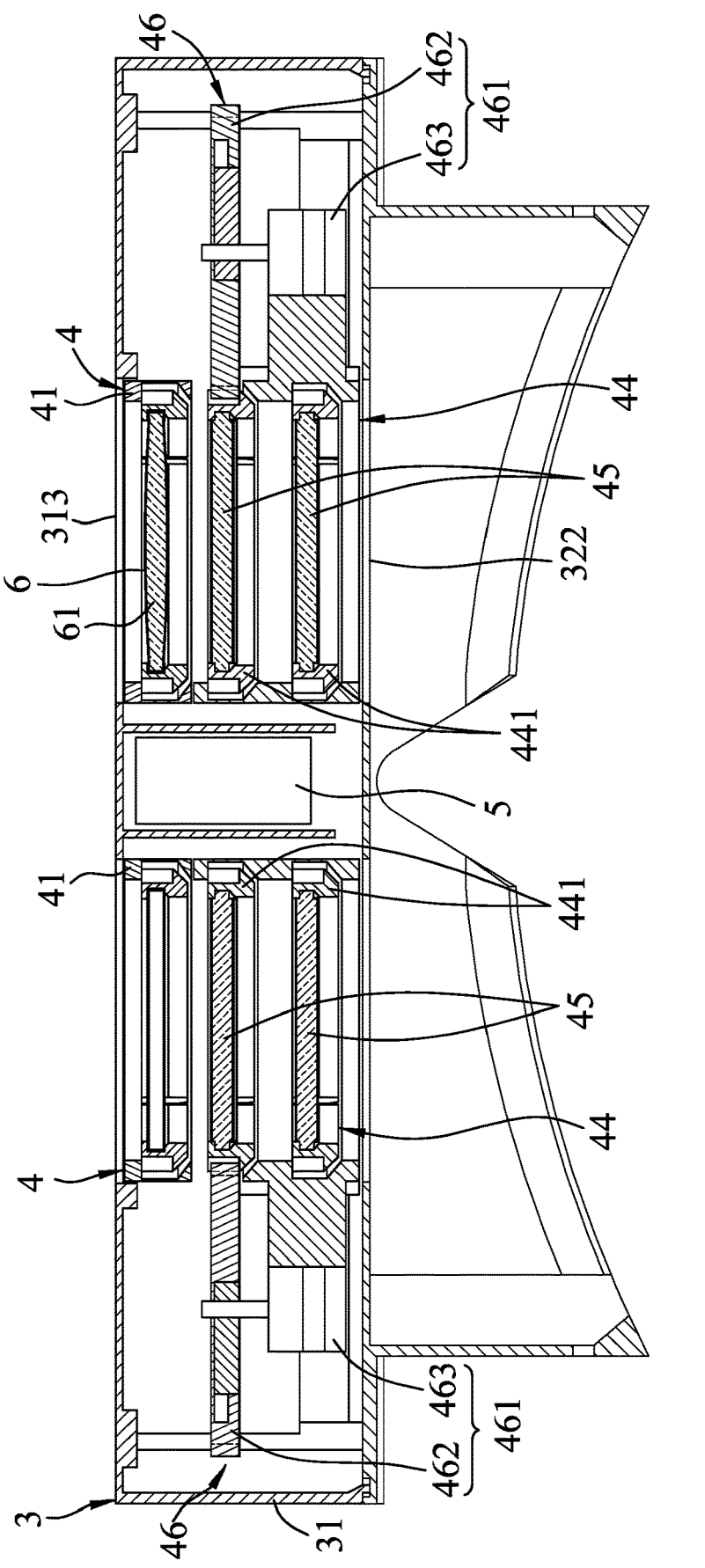
FIG. 19 is a view similar to FIG. 15, but illustrating an alternative form of the second embodiment.

An alternative form of the second embodiment is shown in FIGS. 18 and 19. In this case, the focal length adjusting lens 43 is omitted, and the tubular member 412 of the lens carrier 41 of each lens adjusting unit 4 has three spaced-apart annular grooves 4124. Each insertion hole 317 is aligned with one of the annular grooves 4124 of the tubular member 412 of the lens carrier 41 of the corresponding lens adjusting unit 4. The one of the annular grooves 4124 of the tubular member 412 is proximate to the main front wall 312. The rotary lens holders 441 of the rotary lens holder mechanism 44 are respectively disposed in the other two of the annular grooves 4124. The prisms 45 are respectively received in the rotary lens holders 441 such that the bases thereof are opposite to each other in the top-bottom direction. The rotary lens holders 441 can be driven by the drive module 461 of the drive mechanism 46 to rotate synchronously, so that the prisms 45 can be used to adjust the BI prism power and the BO prism power.

Figure 20:
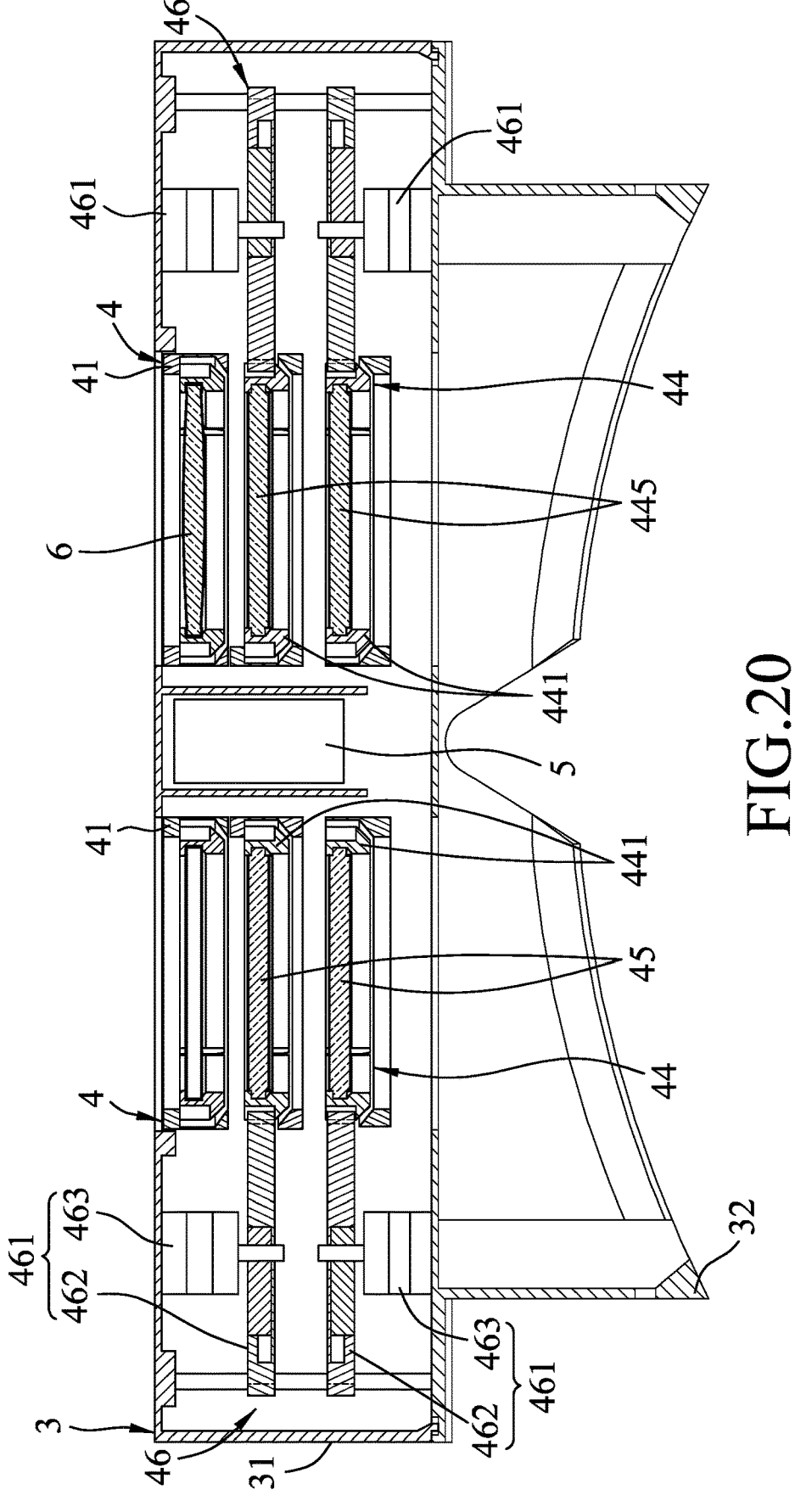
FIG. 20 is a view similar to FIG. 14, but illustrating another alternative form of the second embodiment.

Another alternative form of the second embodiment is shown in FIG. 20, which is similar to that shown in FIG. 19. However, in this case, the drive mechanism 46 of each lens adjusting unit 4 is provided with two drive modules 461, and the rotary lens holder assembly 44 only includes the two rotary lens holders 441, that is, the transmission gear 442 (see FIG. 18) is omitted herein. The drive modules 461 are respectively connected to the rotary lens holders 441, so that each drive module 461 can be separately controlled by the control unit 5 to drive rotation of the respective rotary lens holder 441 and the prism 45 disposed therein. Through this configuration, it is more convenient to rotate and adjust the prisms 45 so that the bases thereof are opposite to each other in the top-bottom direction to thereby provide adjustment of the BI and BO prism diopter states; or, the prisms 45 can be adjusted such that the bases thereof are opposite to each other in the left-right direction to thereby provide adjustment of the BU and BD prism diopter states.

In summary, in the visual examining and training device 200, 200' of this disclosure, through the structural design of the rotary lens holder assembly 44, the prisms 45 and the drive mechanism 46 of each lens adjusting unit 4, the prism power generated by each lens adjusting unit 4 can be automatically and precisely adjusted, and the positive and negative fusion ability of the eye of the user can be accurately detected. Furthermore, training of the muscles of the eyes of the user can be conveniently carried out to strengthen the extraocular muscle contraction and rotation ability of the eyes, and the training data can be accurately quantified.

Moreover, with the focal length adjusting lens 43 mounted in the tubular member 412 of the lens carrier 41 of each lens adjusting unit 4, adjustment force of the muscles around the eye of the user can be relaxed, that is, in the case of relieving the pressure on the ciliary muscle, training of the contraction of the muscles around the eye is performed. In addition, through the structural design of the wearing unit 3 which can provide disposal of the Maddox rod 6 therein, this disclosure can be used to accurately detect horizontal and vertical phoria of the eye, and to measure the degree of strabismus. Therefore, the visual examining and training device 200, 200' of this disclosure is relatively convenient and practical to use, and the object of this disclosure can indeed be achieved.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A visual examining and training device suitable for wearing by a user, comprising:
a wearing unit that is suitable for wearing on a head of the user, that is configured to be disposed in front of the eyes of the user, and that includes a main housing;
two lens adjusting units disposed in said main housing and spaced apart from each other in a left-right direction for the eyes of the user to view an object, each of said lens adjusting units including
a lens carrier including a plate member formed with two through holes spaced apart in the left-right direction, a tubular member extending rearwardly from said plate member at a position corresponding to one of said through holes and defining an inner space communicating and aligned with said one of said through holes, and a support bracket connected to said plate member and said tubular member and corresponding in position to the other one of said through holes,
a rotary lens holder assembly disposed in said inner space of said tubular member,
two prisms coaxially disposed in said rotary lens holder assembly and spaced apart from each other in a front-rear direction,
a focal length adjusting lens disposed in said inner space of said tubular member and spaced apart from said prisms in the front-rear direction for adjusting a focal length of a corresponding one of the eyes of the user, and
a drive mechanism mounted on said support bracket and connected to said rotary lens holder assembly for driving said rotary lens holder assembly together with said prisms to rotate; and
a control unit signally connected to said drive mechanisms of said lens adjusting units and being able to be triggered by a control signal to control the operation of said drive mechanisms;
wherein said tubular member has an upper portion formed with a cutout portion communicating with said inner space and proximate to said plate member, and a mounting seat extending across said cutout portion;
wherein said rotary lens holder assembly includes
two rotary lens holders that are disposed rotatably and coaxially in said inner space of said tubular member, that are spaced apart from each other in the front-rear direction, and that has an outer peripheral surface provided with a plurality of spaced-apart teeth, said rotary lens holders being located at positions corresponding to front and rear sides of said mounting seat, and
a transmission gear rotatably mounted on said mounting seat and meshing with said teeth of said rotary lens holders;
wherein said two prisms are received respectively and fixedly in said rotary lens holders; and
wherein said drive mechanism includes a drive module connected to one of said rotary lens holders and being controllable by said control unit to operate and drive said one of said rotary lens holders to rotate, which in turn, drives the other one of said rotary lens holders to rotate in an opposite direction through said transmission gear, said prisms being respectively driven by said rotary lens holders to rotate therewith in opposite directions.

2. The visual examining and training device as claimed in claim 1, wherein said drive module includes a motor assembly fixed to said support bracket, and a drive gear journalled on a shaft of said motor assembly and meshing with said teeth of said one of said rotary lens holders, said motor assembly being controllable by said control unit to drive rotation of said drive gear.

3. The visual examining and training device as claimed in claim 1, wherein said main housing of said wearing unit is provided with two insertion holes spaced apart in the left-right direction and respectively communicating with said inner spaces of said tubular members of said lens carriers of said lens adjusting units, said visual examining and training device further comprising a Maddox rod removably inserted through one of said insertion holes and positioned in said tubular member of said lens carrier of a corresponding one of said lens adjusting units, said Maddox rod being coaxial with said prisms of the corresponding one of said lens adjusting units.

4. The visual examining and training device as claimed in claim 3, wherein said rotary lens holder assembly includes two rotary lens holders that are disposed rotatably and coaxially in said inner space of said tubular member, that are spaced apart from each other in the front-rear direction, and that receive respectively and fixedly said prisms, said drive mechanism including two drive modules respectively connected to said rotary lens holders, each of said drive modules being controllable by said control unit to operate and drive a respective one of said rotary lens holders to rotate, which in turn, drives a respective one of said prisms to rotate therewith.

5. The visual examining and training device as claimed in claim 4, wherein each of said rotary lens holders has an outer peripheral surface provided with a plurality of spaced-apart teeth, and each of said drive modules includes a motor assembly fixed to said support bracket of said lens carrier of the corresponding one of said lens adjusting units, and a drive gear journalled on a shaft of said motor assembly and meshing with said teeth of said respective one of said rotary lens holders, said motor assembly being controllable by said control unit to drive rotation of said drive gear.

6. The visual examining and training device as claimed in claim 3, wherein:

said tubular member has an upper portion formed with a cutout portion communicating with said inner space and proximate to said plate member, and a mounting seat extending across said cutout portion;

said rotary lens holder assembly includes two rotary lens holders that are disposed rotatably and coaxially in said inner space of said tubular member, that are spaced apart from each other in the front-rear direction, and that has an outer peripheral surface provided with a plurality of spaced-apart teeth, said rotary lens holders being located at positions corresponding to front and rear sides of said mounting seat, and a transmission gear rotatably mounted on said mounting seat and meshing with said teeth of said rotary lens holders;

said two prisms are received respectively and fixedly in said rotary lens holders; and said drive mechanism includes a drive module connected to one of said rotary lens holders and being controllable by said control unit to operate and drive said transmission gear to rotate, which in turn, drives said rotary lens holders to synchronously rotate in opposite directions.

7. The visual examining and training device as claimed in claim 6, wherein said drive module includes a motor assembly fixed to said support bracket, and a drive gear journalled on a shaft of said motor assembly and meshing with said teeth of said one of said rotary lens holders, said motor assembly being controllable by said control unit to drive rotation of said drive gear.

8. The visual examining and training device as claimed in claim 1, wherein said lens adjusting units are movably disposed in said main housing of said wearing unit in the left-right direction.

9. The visual examining and training device as claimed in claim 8, wherein said wearing unit further includes an eye-covering housing disposed rearwardly of said main housing for covering and surrounding the eyes of the user, said main housing being formed with two slots that extend therethrough in a top-bottom direction and that extend in the left-right direction, each of said lens adjusting units further including an adjusting member which has a protruding portion extending from a bottom side of said tubular member and out of a corresponding one of said slots, and an operating portion extending horizontally and rearwardly from a bottom end of said protruding portion, said operating portion being operable to move said protruding portion along the corresponding one of said slots in the left-right direction so as to synchronously drive said lens carrier to move in the left-right direction relative to said main housing.

10. The visual examining and training device as claimed in claim 9, wherein said main housing includes a main front wall having two first view holes extending therethrough in the front-rear direction and respectively corresponding to said lens adjusting units, and a main surrounding wall extending rearwardly from a periphery of said main front wall and cooperating with said main front wall to define a mounting space having an opening that faces rearward, said eye-covering housing including an eye-covering front wall that is connected to a rear side of said main surrounding wall for covering said opening of said mounting space, and an eye-covering surrounding wall extending rearwardly from a rear side of said eye-covering front wall for surrounding the eyes of the user, said eye-covering front wall having two second view holes extending therethrough in the front-rear direction and respectively corresponding to said lens adjusting units.

11. The visual examining and training device as claimed in claim 1, wherein said focal length adjusting lens is a convex lens.

* * * * *